(12) United States Patent
Bae et al.

(10) Patent No.: US 9,017,384 B2
(45) Date of Patent: Apr. 28, 2015

(54) COMPOSITE SPINAL ROD

(75) Inventors: Hyun Bae, Santa Monica, CA (US); Charanpreet S. Bagga, Basking Ridge, NJ (US)

(73) Assignee: Stryker Spine (FR)

( * ) Notice: Subject to any disclaimer, the term of this patent is extended or adjusted under 35 U.S.C. 154(b) by 59 days.

(21) Appl. No.: 12/454,187

(22) Filed: May 13, 2009

(65) Prior Publication Data

US 2009/0287251 A1 Nov. 19, 2009

Related U.S. Application Data

(60) Provisional application No. 61/053,001, filed on May 13, 2008.

(51) Int. Cl.
*A61B 17/70* (2006.01)

(52) U.S. Cl.
CPC ......... *A61B 17/7026* (2013.01); *A61B 17/7028* (2013.01); *A61B 17/7031* (2013.01); *A61B 17/7005* (2013.01); *A61B 17/701* (2013.01); *A61B 17/7014* (2013.01)

(58) Field of Classification Search
USPC ................................................ 606/246–278
See application file for complete search history.

(56) References Cited

U.S. PATENT DOCUMENTS

| | | |
|---|---|---|
| 2,573,050 A | 10/1951 | Orsini |
| 4,237,186 A | 12/1980 | Ingraham |
| 4,369,769 A | 1/1983 | Edwards |
| 4,743,260 A | 5/1988 | Burton |
| 5,002,712 A | 3/1991 | Goldmann et al. |
| 5,059,057 A | 10/1991 | Graef |
| 5,366,773 A | 11/1994 | Schroll et al. |
| 5,393,536 A | 2/1995 | Brandt et al. |
| 5,415,661 A | 5/1995 | Holmes |
| 5,672,175 A | 9/1997 | Martin |
| 5,702,395 A | 12/1997 | Hopf |
| 5,704,936 A | 1/1998 | Mazel |
| RE36,221 E | 6/1999 | Breard et al. |
| 6,003,356 A | 12/1999 | Mills et al. |
| 6,283,998 B1 | 9/2001 | Eaton |
| 6,293,949 B1 | 9/2001 | Justis et al. |

(Continued)

FOREIGN PATENT DOCUMENTS

| | | |
|---|---|---|
| DE | 2821678 | 11/1979 |
| EP | 1574173 A1 | 9/2005 |

(Continued)

OTHER PUBLICATIONS

International Search Report PCT/US2009/003031 end Jun. 30, 2009.

(Continued)

*Primary Examiner* — Kevin T Truong
*Assistant Examiner* — Nicholas Plionis
(74) *Attorney, Agent, or Firm* — Lerner, David, Littenberg, Krumholz & Mentlik, LLP

(57) ABSTRACT

Disclosed is a spinal rod that includes an elongated flexible component and a reinforcing component. The reinforcing component is resistant to damage from compressive forces. The reinforcing component may be disposed circumferentially around at least a portion of the flexible component so as to define at least one compression slot. The reinforcing element may include an upper bracket, an opposing lower bracket, and a connecting pin extending therebetween.

16 Claims, 25 Drawing Sheets

(56) References Cited

U.S. PATENT DOCUMENTS

| | | |
|---|---|---|
| 6,413,257 B1 | 7/2002 | Lin et al. |
| 6,569,201 B2 | 5/2003 | Moumene et al. |
| 6,602,293 B1 | 8/2003 | Biermann et al. |
| 6,758,862 B2 | 7/2004 | Berry et al. |
| 6,776,945 B2 | 8/2004 | Chin et al. |
| 6,783,527 B2 | 8/2004 | Drewry et al. |
| 6,855,422 B2 | 2/2005 | Magill et al. |
| 6,921,264 B2 | 7/2005 | Mayer et al. |
| 6,966,910 B2 | 11/2005 | Ritland |
| 6,986,771 B2 | 1/2006 | Paul et al. |
| 6,989,011 B2 | 1/2006 | Paul et al. |
| 7,083,622 B2 | 8/2006 | Simonson |
| 7,125,410 B2 | 10/2006 | Freudiger |
| 7,137,985 B2 | 11/2006 | Jahng |
| 2002/0107570 A1 | 8/2002 | Sybert et al. |
| 2003/0191470 A1 | 10/2003 | Ritland |
| 2003/0203695 A1 | 10/2003 | Polanco et al. |
| 2003/0220642 A1 | 11/2003 | Freudiger |
| 2003/0220643 A1 | 11/2003 | Ferree |
| 2004/0049190 A1 | 3/2004 | Biedermann et al. |
| 2004/0092934 A1 | 5/2004 | Howland |
| 2004/0172025 A1 | 9/2004 | Drewry et al. |
| 2004/0215191 A1 | 10/2004 | Kitchen |
| 2004/0215341 A1 | 10/2004 | Sybert et al. |
| 2004/0236327 A1 | 11/2004 | Paul et al. |
| 2004/0236328 A1 | 11/2004 | Paul et al. |
| 2004/0267260 A1 | 12/2004 | Mack et al. |
| 2005/0033295 A1 | 2/2005 | Wisnewski |
| 2005/0065515 A1 | 3/2005 | Jahng |
| 2005/0065516 A1 | 3/2005 | Jahng |
| 2005/0085814 A1 | 4/2005 | Sherman et al. |
| 2005/0085815 A1 | 4/2005 | Harms et al. |
| 2005/0101956 A1 | 5/2005 | Simonson |
| 2005/0124991 A1 | 6/2005 | Jahng |
| 2005/0131407 A1 | 6/2005 | Sicvol et al. |
| 2005/0143823 A1 | 6/2005 | Boyd et al. |
| 2005/0149020 A1 | 7/2005 | Jahng |
| 2005/0154390 A1 | 7/2005 | Biedermann et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0182400 A1 | 8/2005 | White |
| 2005/0182401 A1 | 8/2005 | Timm et al. |
| 2005/0182409 A1 | 8/2005 | Callahan et al. |
| 2005/0192574 A1* | 9/2005 | Blain ............................ 606/61 |
| 2005/0203513 A1 | 9/2005 | Jahng et al. |
| 2005/0203517 A1 | 9/2005 | Jahng et al. |
| 2005/0234454 A1* | 10/2005 | Chin ............................ 606/61 |
| 2005/0261686 A1 | 11/2005 | Paul |
| 2005/0277926 A1* | 12/2005 | Farris ............................ 606/61 |
| 2005/0283244 A1 | 12/2005 | Gordon et al. |
| 2006/0009768 A1 | 1/2006 | Ritland |
| 2006/0041259 A1 | 2/2006 | Paul et al. |
| 2006/0129147 A1 | 6/2006 | Biedermann et al. |
| 2006/0142760 A1 | 6/2006 | McDonnell |
| 2006/0195093 A1 | 8/2006 | Jahng |
| 2006/0212033 A1 | 9/2006 | Rothman et al. |
| 2006/0212118 A1 | 9/2006 | Abernathie |
| 2006/0229612 A1 | 10/2006 | Rothman et al. |
| 2007/0100341 A1 | 5/2007 | Reglos et al. |
| 2007/0123871 A1 | 5/2007 | Jahng |
| 2007/0233064 A1 | 10/2007 | Holt |
| 2007/0233073 A1 | 10/2007 | Wisnewski et al. |
| 2007/0233095 A1 | 10/2007 | Schlaepfer |
| 2007/0270821 A1 | 11/2007 | Trieu et al. |
| 2007/0282442 A1 | 12/2007 | Malandain et al. |
| 2008/0021469 A1 | 1/2008 | Holt |
| 2008/0091214 A1* | 4/2008 | Richelsoph .................. 606/103 |
| 2008/0161854 A1 | 7/2008 | Bae et al. |
| 2008/0183211 A1* | 7/2008 | Lamborne et al. ........... 606/249 |
| 2008/0183212 A1 | 7/2008 | Veldman et al. |
| 2009/0177231 A1* | 7/2009 | Kiester ......................... 606/252 |
| 2009/0177232 A1* | 7/2009 | Kiester ......................... 606/260 |
| 2010/0069964 A1* | 3/2010 | Lechmann .................... 606/278 |

FOREIGN PATENT DOCUMENTS

| | | |
|---|---|---|
| FR | 2799949 | 4/2001 |
| JP | 11-501235 | 2/1999 |
| JP | 2005253971 A | 9/2005 |
| JP | 2007506514 A | 3/2007 |
| WO | WO-9732533 | 9/1997 |
| WO | WO-2004105577 | 12/2004 |
| WO | 2005030031 A2 | 4/2005 |
| WO | WO-2006063107 | 6/2006 |
| WO | 2006096241 A2 | 9/2006 |
| WO | WO-2006096414 | 9/2006 |
| WO | 2007038429 A1 | 4/2007 |
| WO | 2007070757 A2 | 6/2007 |
| WO | WO-2007097905 | 8/2007 |
| WO | 2007136612 A2 | 11/2007 |

OTHER PUBLICATIONS

Extended European Search Report for Application No. 09746988 dated Jan. 7, 2013.

* cited by examiner

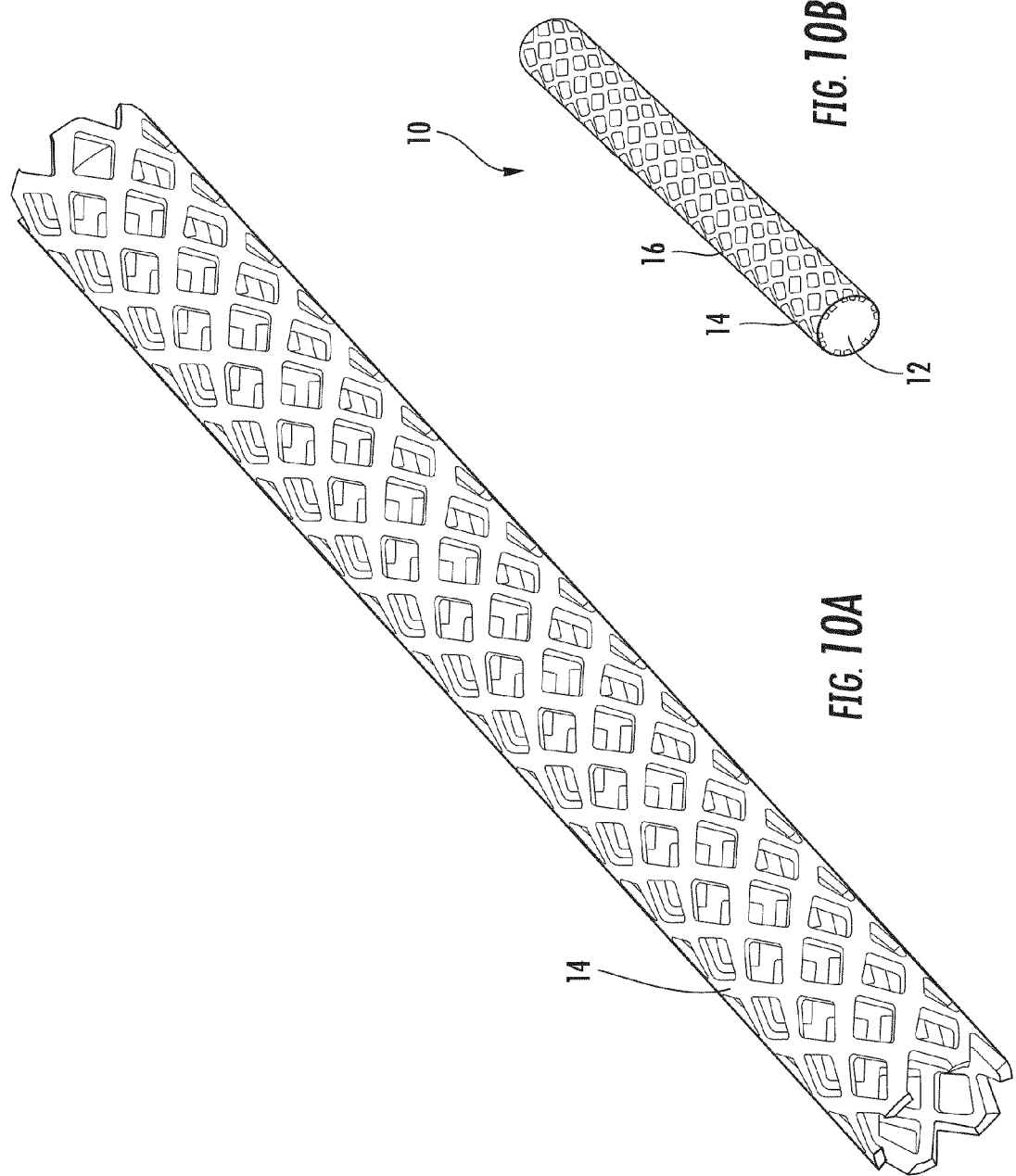

COMPOSITE SPINAL ROD

CROSS-REFERENCE TO RELATED APPLICATIONS

This application claims the benefit of the filing date of U.S. Provisional Patent Application No. 61/053,001 filed May 13, 2008, the disclosure of which is hereby incorporated herein by reference.

FIELD OF THE INVENTION

The present technology relates to orthopedic surgery. In particular, the present technology relates to a spinal rod formed of a reinforcing component and a flexible component so as to provide a combination of flexibility, strength, and resistance to localized compressive forces. More particularly, the present technology provides a titanium and polyetheretherketone (PEEK) composite rod that can be manufactured in a variety of configurations designed to provide different degrees of flexibility and stiffness as desired.

BACKGROUND OF THE INVENTION

Spinal or vertebral rods are often used in the surgical treatment of spinal disorders such as degenerative disc disease, disc herniation, scoliosis or other curvature abnormalities or fractures. Spinal rods, which may be mechanically anchored to sequentially aligned pedicle screw assemblies connected to vertebral bodies, serve to provide rigidity to portions of the spinal column to encourage the vertebral bodies to fuse after spinal-fusion surgery. Fusion results in the permanent immobilization of one or more of the intervertebral joints between vertebral bodies. To achieve spinal fusion the spinal rods selected are typically uniform along the entire length of the rod and manufactured from a single or integral piece of relatively inflexible material having a uniform diameter and sized to provide substantially rigid support to the spinal construct.

Fusion, however, can have some very undesirable side effects. Spinal fusion by design results in immobilization of a portion of the spine and thus can severely limit the natural motion of the subject. Further, although fusion can result in a strengthened portion of the spine, it may also result in more rapid degeneration and even hyper-mobility and collapse of other portions of the spine that are adjacent to the portion of the spine being fused.

An alternative to the use of rigid spinal rods is the use of flexible or dynamic spinal rods to create a more normal loading pattern in flexion, extension, distraction, compression, side bending and torsion. The efforts to provide a dynamic spinal rod conventionally involve the use of flexible materials that are capable of providing the needed bending and twisting dynamics, but these materials can lack the necessary strength to avoid the damage that can result from the compressive forces of bone screw attachments to the spinal rods.

Recent attempts to provide dynamic spinal rods typically include the use of a rod formed of flexible plastic material, such as polyurethane, UHMW polyethylene, PEEK or Teflon. Efforts to include a measured degree of reinforcement to such flexible rods have employed longitudinally aligned reinforcing components that extend internally through the length of the flexible rods, the reinforcing components being formed of materials such as Kevlar, polyethylene, polyurethane, Teflon fiber, carbon fiber, or stainless steel. Common to all current attempts to provide a flexible spinal rod is the potential failure of such rods to provide flexibility while being sufficiently strong and resistant to the damaging compressive forces of attached bone screws.

There exists therefore a need to provide a flexible spinal rod that is capable of being secured with conventional bone screws without being susceptible to damage from the compressive forces at the attachment point of the bone screws.

BRIEF SUMMARY OF THE INVENTION

The present technology meets the above identified need by providing a spinal rod that may be sufficiently flexible to provide a dynamic connecting rod between adjacent vertebrae while maintaining sufficient surface strength to avoid damage from the normal compressive forces associated with the attachment of bone screws to the rod.

Also provided is a spinal rod having a composite construction that may include flexible materials allowing for dynamic control of the spine and may also include compressive force resistant materials that are sufficiently provided in the composite rod at the surface of the rod so as to be the contact point for any attachments or bone screws.

Also provided is a spinal rod of composite construction that may include a flexible material component and an embedded reinforcing component disposed at least partially on the surface of the spinal rod at points where bone screws can be attached. The flexible component may be a material such as PEEK and the reinforcing component material may be a metallic compression resistant material such as titanium.

Also provided is a composite construction spinal rod wherein compressive forces applied to the surface of the rod may be transferred transversely through the rod by compressive force resistant reinforcing materials so as to protect the flexible component of the rod from damage.

Also provided is a spinal rod having a flexible core material with embedded compression resistant reinforcing components at least partially exposed on the surface of the spinal rod at locations for bone screw attachment. The reinforcing components may extend transversely through the flexible core so as to connect the surfaced exposed reinforcing material on one side of the spinal rod to the surface exposed reinforcing material on at least one other side of the spinal rod.

Also provided is a spinal rod constructed of a combination of a flexible component and a reinforcing component, wherein the reinforcing component may be provided at multiple levels of the spinal construct.

Also provided is a spinal rod constructed of a combination of a flexible component and a reinforcing component, wherein the flexible component may be manufactured to have a selected gradient flexibility along the length of the spinal rod.

Also provided is a spinal rod constructed of a combination of a flexible component and a reinforcing component, wherein the reinforcing component may be configured to also provide a connecting function between two separate flexible rod components aligned end to end, the two separate flexible rod components being of the same construction or of different construction and thereby having the same flexibility or different flexibilities one to the other.

Also provided is a spinal rod with reinforcing components exposed on at least a portion of the surface of the flexible component and connecting pins extending transversely through the flexible component core so as to closely approach but not directly contact the undersurface of at least one of the opposing surface exposed reinforcing components to define a compression space therebetween. Thus, compressive forces on one of the surface exposed reinforcing components may first serve to close the compression space and cause contact of that reinforcing component to the underlying connecting pin so as to transfer the compressive force through the connecting pin to the reinforcing component on the opposing side of the rod.

Also provided is a method of implanting a spinal construct that allows a degree of flexibility and controlled motion between adjacent vertebrae while maintaining sufficient strength on the surface of the spinal connecting rod to avoid damage from the compressive forces exerted by conventional bone screw attachments.

Also provided is a kit containing at least one spinal rod having both flexible characteristics and surface strength needed to avoid damage from the externally applied compressive forces and at least two bone screws.

One aspect of the technology provides a spinal rod including an elongated flexible component and a reinforcing component, the reinforcing component being resistant to damage from compressive forces. The reinforcing component may be disposed circumferentially around at least a portion of the flexible component so as to define at least one compression slot.

In one embodiment, the spinal rod reinforcing element of the spinal rod may be disposed circumferentially around at least a portion of the flexible component so as to define a space between the flexible component and the reinforcing component. Furthermore, the reinforcing component may include a screw contact surface configured to facilitate contact with an attachment. The contact surface may be treated so as to facilitate contact with a pedicle screw.

In addition, the reinforcing component of the spinal rod may be at least two separate reinforcing elements and may be at least partially embedded in the surface of the flexible component. Furthermore, the flexible component may have a gradient of flexibility along at least a portion of its length. In addition or alternatively, the flexible component may have a plurality of sections where the flexibility of one section differs from the flexibility of at least one other section.

Another aspect of the technology provides a spinal rod that includes an elongated flexible component and a reinforcing component, where the reinforcing component being resistant to damage from compressive forces. In addition, the reinforcing element may comprise an upper bracket, an opposing lower bracket, and a connecting pin extending therebetween.

In one embodiment, the connecting pin may be disposed transversely through the flexible component, each end of the connecting pin being directed toward the upper bracket or the lower bracket, with at least one of the upper bracket and the connecting pin or the lower bracket and the connecting pin defining a compression space. Furthermore, at least one of the upper bracket and the lower bracket may be at least partially embedded in the surface of the flexible component.

In a further embodiment, at least one edge of the upper and lower bracket may be tapered, and the tapered edge may create a gradient of compressive stress shielding for the underlying flexible component. Furthermore, the flexible component may have a gradient of flexibility along at least a portion of its length. Still further, the reinforcing component may be at least two separate reinforcing elements and the flexible component may have a plurality of sections, where the flexibility of one section differs from the flexibility of at least one other section.

A further aspect of the present technology provides a method for connecting and stabilizing adjacent vertebrae, the method including the steps of providing the a spinal rod of the present technology, providing a surgical field of view for insertion of the spinal rod, and connecting the spinal rod to adjacent vertebrae. Furthermore, the connecting step may further include connecting pedicle screws to vertebrae and connecting the pedicle screws to the spinal rod. The pedicle screws may be connected to the spinal rod at a position on the spinal rod where compressive forces imposed by the pedicle screws on the spinal rod are transferred via the reinforcing component transversely across the flexible component, wherein the reinforcing component provides stress shielding for the flexible component.

Yet another aspect of the present technology provides a kit for use in connecting and stabilizing adjacent vertebrae, the kit including at least one spinal rod according to the present technology and at least one pedicle screw. In the kit, the at least one spinal rod may be multiple spinal rods and the at least one pedicle screw may be multiple pedicle screws. In addition, the kit may further include at least one instrument or tool associated with the use of the spinal rods and the pedicle screws.

An alternative embodiment of the present technology provides a spinal rod, the spinal rod including an elongated flexible component and a reinforcing component, the reinforcing component being resistant to damage from compressive forces. Furthermore, a portion of the reinforcing component may be circumferentially disposed on the surface of the flexible component and a portion of the reinforcing component may extend transversely through the flexible component to connect opposing sides of the circumferentially disposed reinforcing component one to the other, wherein the reinforcing component is capable of stress shielding the flexible component from compressive force damage by transferring externally applied compressive forces transversely across the elongated flexible component to the opposing side of the spinal rod. This portion of the reinforcing component of this embodiment may be multiple portions. In addition, the reinforcing component may be configured as a plurality of circumferentially disposed rings, at least one of the rings having multiple portions extending transversely through the flexible component. Furthermore, the multiple transversely extending portions may be symmetrically disposed passing transversely through the flexible component. Alternatively, the multiple transversely extending portions may be asymmetrically and selectively disposed so as to make the spinal rod capable of greater flexibility in selected planes of movement of the flexible component.

Another embodiment of the present technology provides a spinal rod including an elongated flexible component and a reinforcing component, where the reinforcing component may be resistant to damage from compressive forces and wherein the reinforcing element is configured on the flexible component as a circumferentially disposed spiral extending along at least a portion of the elongated flexible component of the spinal rod.

Yet another embodiment provides a spinal rod including an elongated flexible component and a reinforcing component, with the reinforcing component being resistant to damage from compressive forces and wherein the reinforcing component may be configured to provide a protective end cap on at least one end of the elongated flexible component.

Alternatively, an embodiment of the present technology may provide a spinal rod including an elongated flexible component and a reinforcing component, with the reinforcing component being resistant to damage from compressive forces and wherein the reinforcing component is configured as a plurality of elongated reinforcing elements disposed on the surface of the elongated flexible component and extending parallel to the longitudinal axis of the elongated flexible component.

One embodiment of the present technology provides a spinal rod including an elongated flexible component and a reinforcing component, with the reinforcing component being resistant to damage from compressive forces and wherein the flexible component comprises a carbon fiber reinforcing structure. The carbon fiber may be chopped or wound. Furthermore, the carbon fiber may be selectively disposed in the flexible component so as to create a gradient of flexibility in the elongated flexible component. The selective disposition of carbon fiber may consist of increased or decreased concentration of chopped carbon fibers, wherein portions of the flexible component having increased chopped carbon fibers may be stiff relative to portions of the flexible component having decreased concentrations of carbon fibers. Furthermore, the selective disposition of carbon fiber may be increased or decreased numbers of winds of wound carbon fibers, wherein portions of the flexible component having increased winds of carbon fibers may be stiff relative to portions of the flexible component having decreased winds of carbon fibers.

One embodiment of the present technology includes a spinal rod, the spinal rod including an elongated flexible component and a reinforcing component, the reinforcing component being resistant to damage from compressive forces and comprising a mesh circumferentially disposed on at least a portion of the surface of the flexible component. In an alternative embodiment, the reinforcing component may comprise a connecting bracket having an upper bracket and an opposing lower bracket, the connecting bracket being configured to connect two separate, longitudinally aligned elongated flexible components to each other end-to-end.

In an alternative embodiment, the spinal rod may include an elongated flexible component, a reinforcing component, and a connecting bracket, the reinforcing component being resistant to damage from compressive forces, and the connecting bracket including at least two transversely disposed connecting pins, each of the pins passing respectively through the flexible component of a respective elongated flexible component of a separate spinal rod.

In yet another embodiment, the spinal rod may have an elongated flexible component and a reinforcing component, the reinforcing component being resistant to damage from compressive forces. In addition, the reinforcing component may be disposed adjacent to at least a portion of the flexible component so as to define at least one compression slot and the reinforcing element may comprise an upper bracket, an opposing lower bracket, and a connecting pin extending therebetween.

BRIEF DESCRIPTION OF THE DRAWINGS

The foregoing and other features of the disclosed technology will become apparent to one skilled in the art to which the present technology relates upon consideration of the following description of exemplary embodiments with reference to the accompanying drawings, wherein:

FIG. 10A-B show an alternative reinforcing component of the spinal rod configured as a tubular mesh and in FIG. 10B disposed around the surface the flexible portion of the rod;

DETAILED DESCRIPTION

Figure 1A:
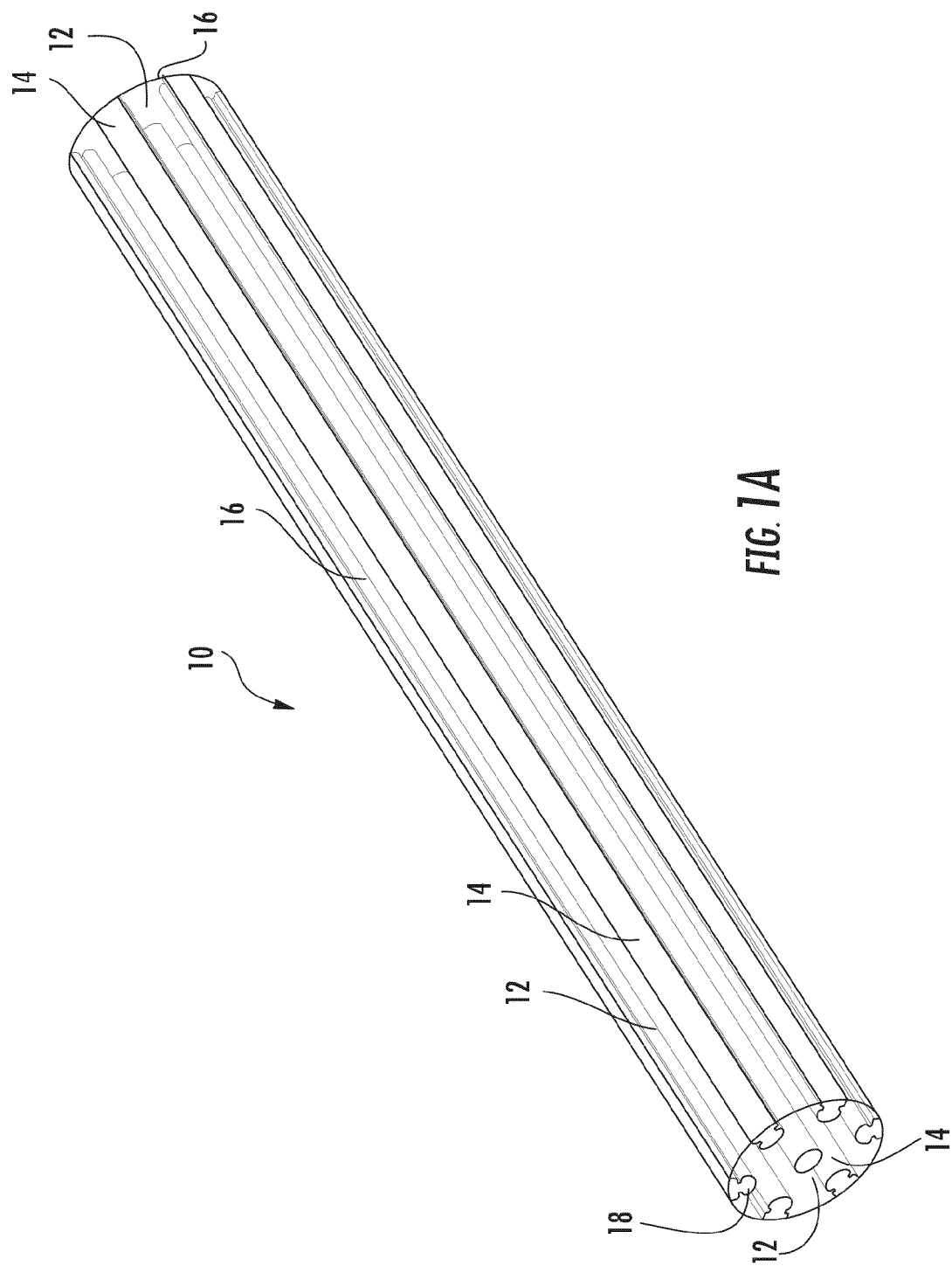
FIG. 1A shows the spinal rod having a flexible component with a generally circular cross section and a plurality of partially embedded rigid reinforcing components.

Preferred embodiments of the present invention are disclosed herein; however, it is understood that the following description and each of the accompanying figures are provided as being exemplary of the invention herein, which may be embodied in various forms without departing from the scope of the claims. Thus, the specific structural and functional details provided in the following description are non-limiting, but serve merely as a basis for the invention as defined by the claims provided herewith. The device described below can be modified as needed to conform to further development and improvement of materials without departing from the invention as claimed.

Referring now to the drawings, wherein like reference numerals indicate similar features, the spinal rod, generally shown at 10 in FIGS. 1A-C, 2A-D, 3B, 4B-D, 4F, 5, 6, 7, 9 and 10B includes an elongate flexible component 12 and at least one rigid reinforcing component 14, the at least one rigid reinforcing component 14 being at least partially exposed on at least a portion of the outer surface 16 of the flexible component 12.

The spinal rod 10 in accordance with the present invention may be used in connection with any suitable components in connection with fusion or other spinal or orthopedic procedures. Such components include pedicle screw assemblies such as those described in U.S. Pat. Nos. 6,261,287; 6,537,276; 6,858,030; and 7,128,743; the disclosures of each being incorporated herein by reference as if fully set forth herein.

Figure 1B:
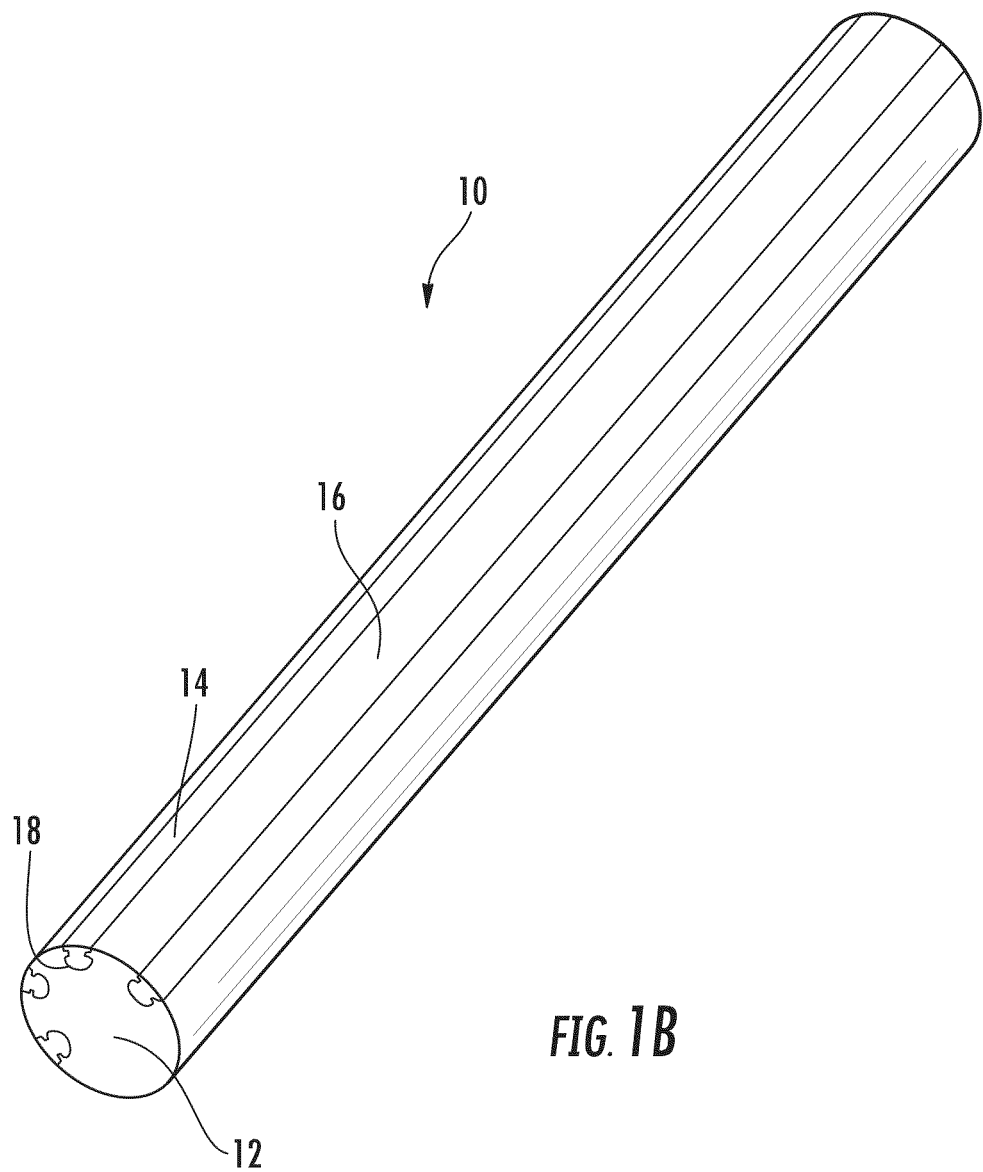
FIG. 1B shows the spinal rod of FIG. 1A having an asymmetrical disposition of partially embedded rigid reinforcing components.
Figure 1C:
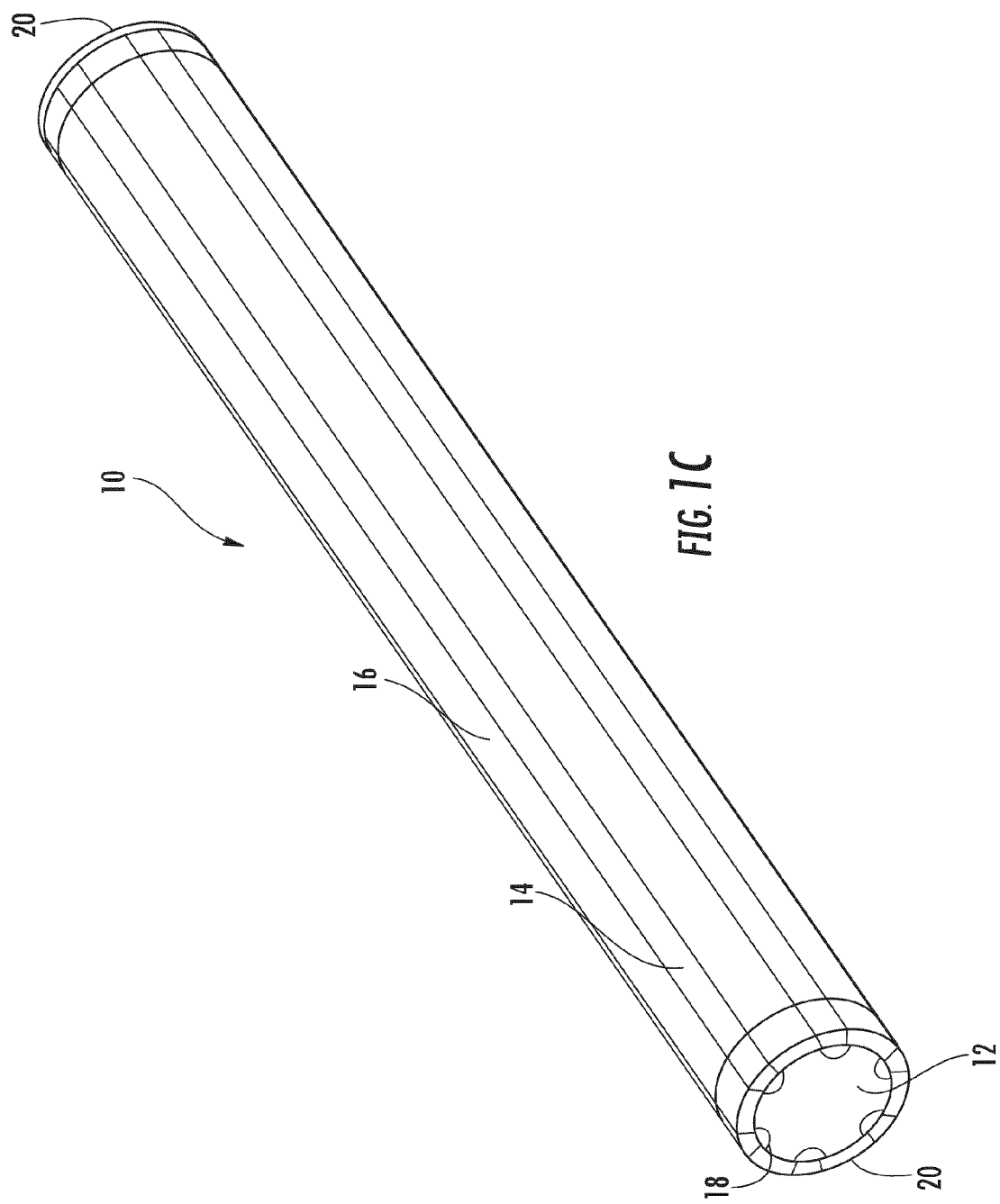
FIG. 1C shows the spinal rod of FIG. 1A having concentric reinforcing component connecting rings partially embedded at each end of the elongate spinal rod.
Figure 9:
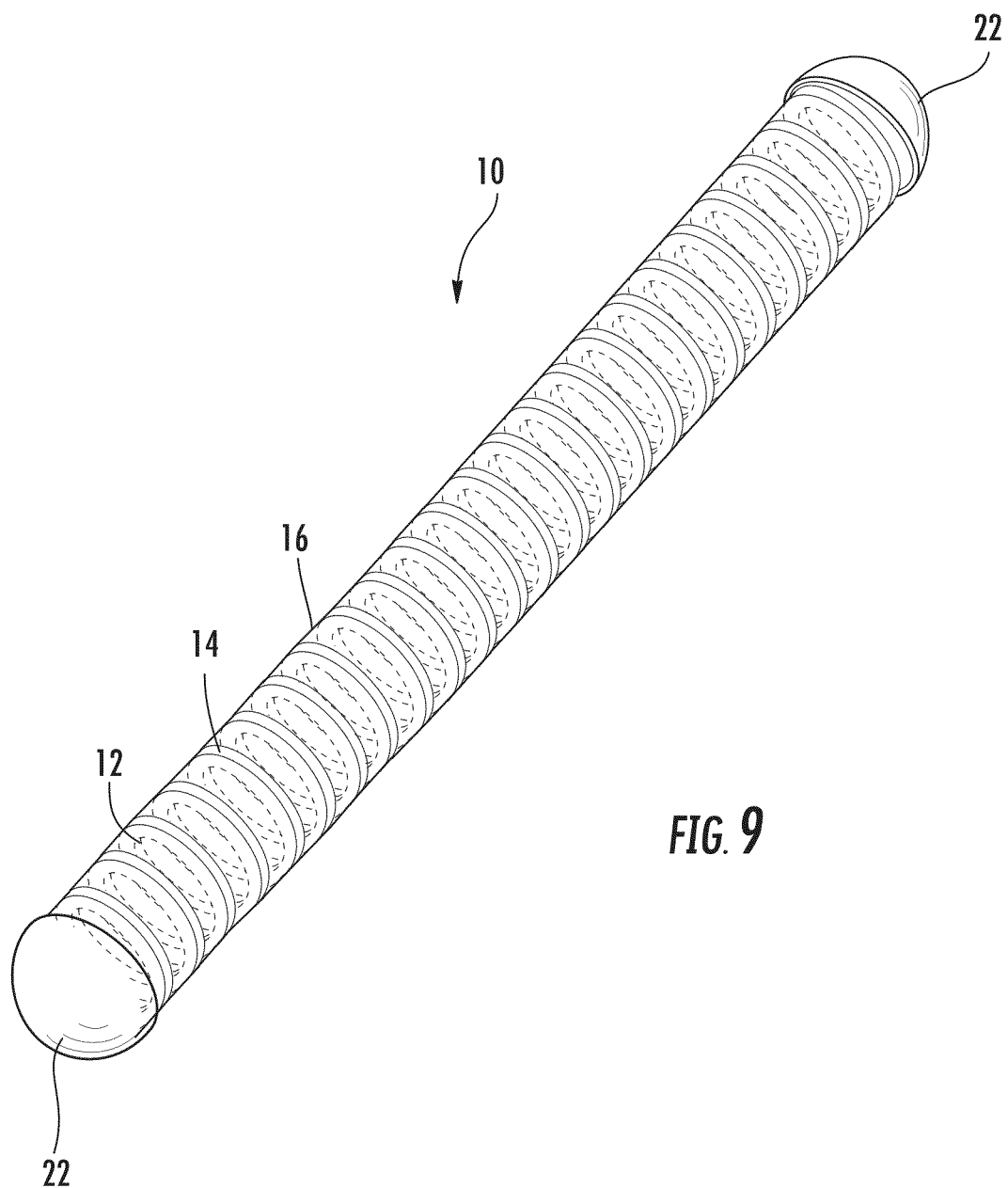
FIG. 9 shows an alternative embodiment of the spinal rod, wherein the reinforcing component is configured in a coil spring like manner and overlaid around the circumference for the full length of the flexible portion of the rod. Alternatively, the flexible portion of the rod may be configured with corresponding recesses on the surface of the flexible portion.

As shown in FIGS. 1A-C, 2A-C, 3B, 4B-D, 4F, 5, 6, 7, 9 and 10B, the reinforcing component 14, while at least partially exposed on the surface of the flexible component 12 may also be at least partially embedded in the flexible component 12 of the spinal rod 10. The reinforcing component 14 may be manufactured of titanium or titanium alloy. However, the reinforcing component 14 may be made of any metal or other suitable material (e.g., ceramic) that is biocompatible and possess sufficient strength to resist damage from the compressive forces associated with the attachment of conventional bone screws to spinal rods. As shown in FIGS. 1A-C, the embedded portion of the reinforcing component 14 may be configured to include retention elements 18, which may serve to support the integrity of the composite construction of the spinal rod 10. As shown in FIG. 1C, the spinal rod 10 may be provided with an end collar 20 or, as shown in FIG. 9, an end cap 22.

The spinal rod 10 may benefit from the bendable nature of the flexible component 12 so as to provide a flexible or dynamic spinal rod as an alternative to the conventional rigid rods typically used in spinal fusion procedures. The flexibility of such a dynamic rod allows selectively controlled articulation of the spine while providing a necessary degree of control for a diseased or injured part of the spine. The reinforcing components 14 may be disposed within the composite spinal rod 10 in a variety of configurations and, as demonstrated in FIG. 1B can be asymmetrically arranged or skewed so as to influence or limit the amount of flexibility along one or more planes about which the vertebrae normally may articulate.

The spinal rod 10 may also be manufactured using a variety of materials, diameters, number, position, and design of reinforcing components 14 to plan and control the degree of flexibility permitted. Indeed, it is not necessary that the spinal rod 10 be cylindrical. Other shapes, such as a hexagonal profile, an oval profile, or any other suitable profile, are also contemplated. There may be a varying of profiles along the length of the spinal rod 10 as well. This can be for many purposes, including variability of stiffness or accommodation of different materials along the length.

In addition, the reinforcing components 14, being at least partially exposed on the outer surface 16 of the flexible component 12, may provide the protection for the spinal rod 10 from the compressive forces that are normally exerted against a spinal rod by the attachment of pedicle bone screws to the rod. Conventional flexible spinal rods, some of which are composed of fragile, flexible, polyurethane, PEEK, or similar materials, typically are damaged and crushed under the compressive forces of the locking set screws used in pedicle or bone screws. Conventional spinal rods having internal reinforcing components may also be subject to the compressive force damage caused by pedicle screw attachment to the external surface of such flexible spinal rods. The damage done to conventional flexible spinal rods in this manner may quickly compromise the integrity of the spinal rod and thus compromise the desired outcome of the original surgical procedure.

The spinal rod 10 may be manufactured using a wide variety of configurations to achieve the goal of providing a flexible or dynamic spinal rod that is not subject to structural damage as a result of the attachment of bone screws. While it is possible to manufacture the flexible component 12 of the spinal rod 10 from a variety of flexible materials known in the art, it may be advantageous to manufacture the flexible component 12 from any of several grades of PEEK. The spinal rod 10 may thus be manufactured to have a wide variance of flexibility to meet the specific needs for the patient. It is also within the concept of the technology to employ carbon fiber reinforced PEEK to increase the strength and durability of the flexible component 12. With PEEK and similar materials, the flexibility of the rod can be varied along the length of a given rod, with or without reinforcing or other components, such that a portion or portions are more flexible than another portion or other portions. For example, the middle of a rod may be made more stiff than the ends.

Figure 2A:
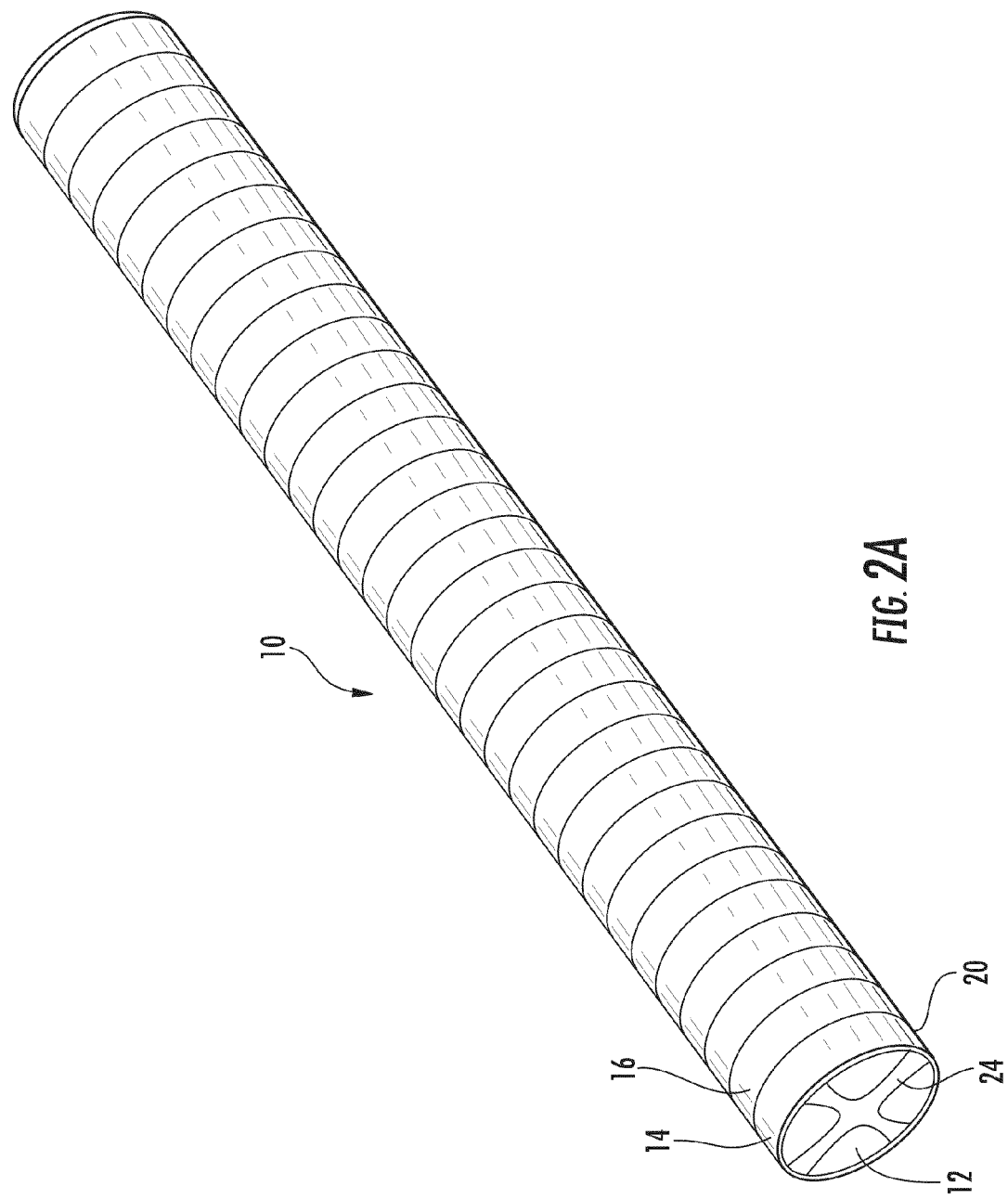
FIG. 2A shows the spinal rod having a flexible component with a generally circular cross section and a plurality of partially embedded rigid reinforcing components disposed in a generally uniform and parallel manner circumferentially along the longitudinal axis of the rod. Also shown is an alternative element of inwardly directed cross members that may bisect each of the reinforcing component rings.

As shown in FIG. 2A, the design of the rod may be a generally circular cross section of the flexible component 12 having a plurality of partially embedded rigid reinforcing components 14 that are arranged in a generally uniform and substantially parallel manner circumferentially around the long axis of the spinal rod. Any variation of such a circumferentially disposed array or spiral of reinforcing components 14 may provide protection for the underlying flexible component 12 by hoop stress transfer around the circumference of the spinal rod 10.

To further facilitate the transfer of compressive forces from any bone screw attached to the spinal rod 10, the reinforcing component rings may be provided with inwardly directed cross members 24 that transversely bisect the flexible component along at least one plane. Such internally directed cross members 24 may function much like supporting trusses to provide axial stress transfer from a reinforcing component 14 portion on one side of the spinal rod 10 to the opposing side of the spinal rod 10. As shown in FIG. 2A, the spinal rod 10 may be provided with multiple cross members 24, that may be perpendicularly arranged relative to each other or alternatively can be of any relative angle to each other. Such variances in relative angle of multiple cross members 24, in addition to providing protection for the internally disposed flexible component 12, may also be advantageously used to strengthen the spinal rod along selected planes to help control the degree and direction of flexibility of the rod 10. Reinforcing components 14 may also be modified to achieve desired strength and stiffness by, for example, connecting the reinforcing components 14 together.

Figure 2B:
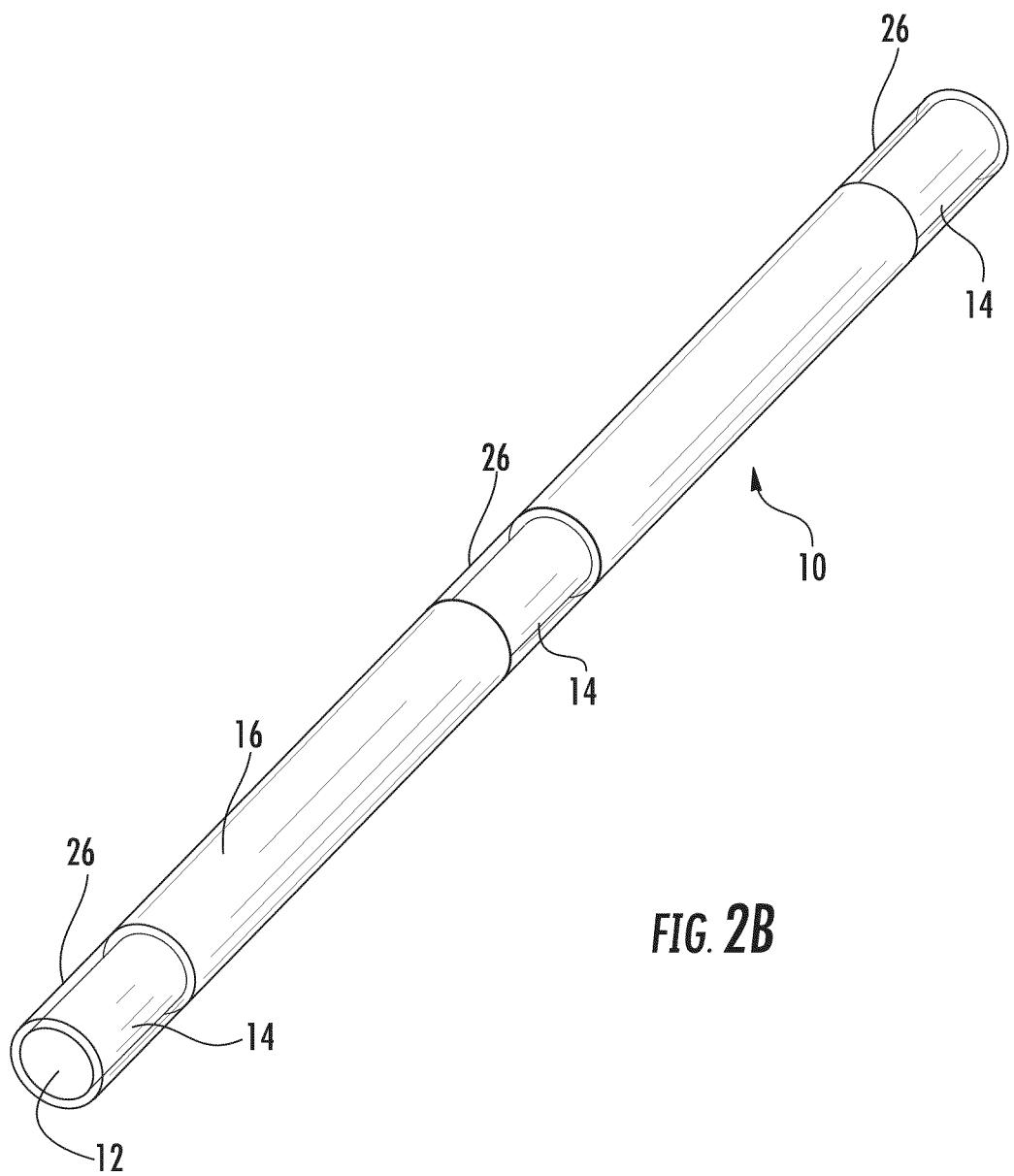
FIG. 2B shows the spinal rod having a similar construction to that of FIG. 2A with the reinforcing rings elongated and disposed along the longitudinal axis of the rod at select locations where bone screw attachment is to be made. This configuration can alternatively also include the element of inwardly directed cross members described and shown in FIG. 2A.

There are contemplated a variety of alternative embodiments that may employ reinforcing components configured as collars 26. Nonlimiting examples of different types of collars 26 are shown in FIGS. 2A-D, 3A-B, and 10D. The collars 26 may be uniformly disposed along the longitudinal axis of the spinal rod 10, as demonstrated in FIG. 2A. Alternatively, the collars 26, as shown in FIG. 2B, may be manufactured so as to be positioned only at those points along the length of the spinal rod 10 where the compressive forces of set screws for bone screw attachment to the spinal rod 10 will be exerted.

Figure 2C:
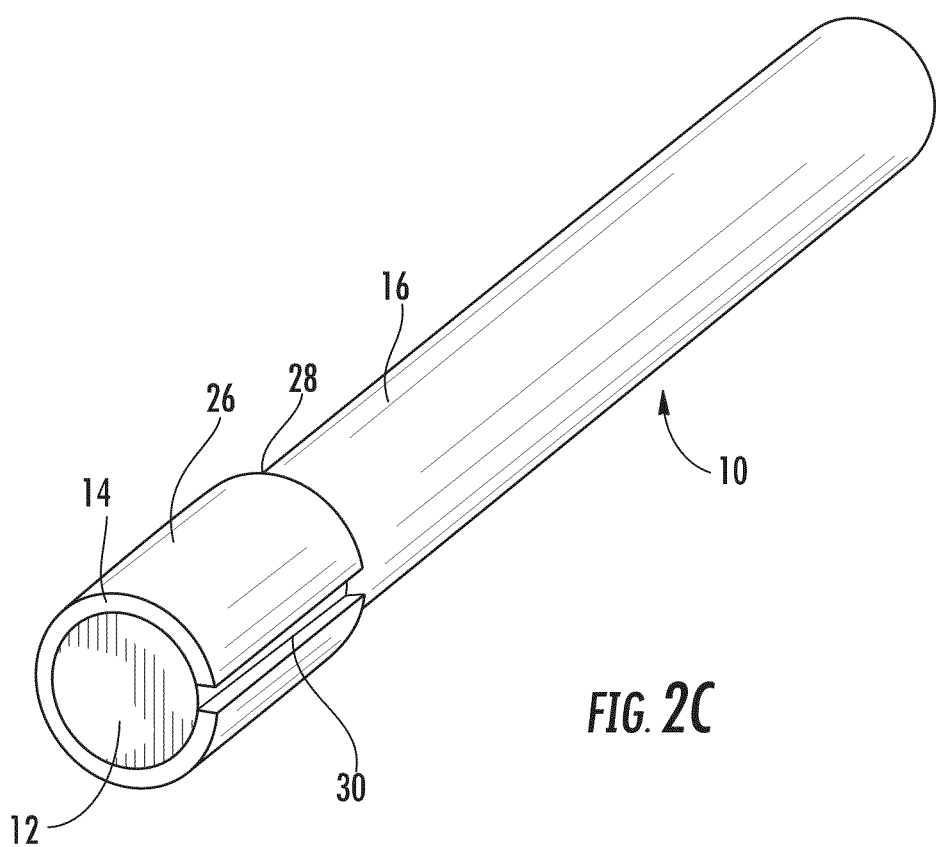
FIG. 2C shows a variation of the spinal rod of FIG. 2B, having reinforcing rings configured to be elevated above the surface of the flexible portion of the spinal rod. Also shown is an alternative element of a compression slit defined in the reinforcing ring.
Figure 2D:
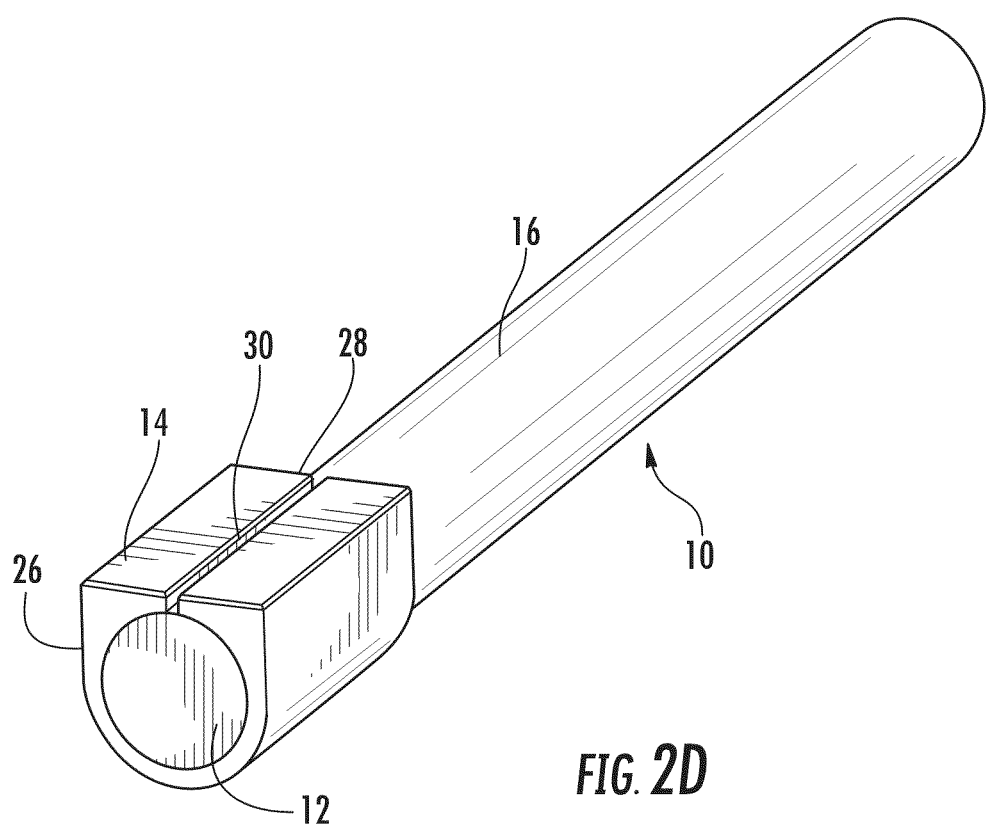
FIG. 2D shows the spinal rod of FIG. 2C wherein the elevated reinforcing component ring is flattened on an upper surface to facilitate contact with the locking set screw of a conventional bone screw which may be attached at that position. Also shown is an alternative element of a compression slit defined in the reinforcing ring.
Figure 3A:
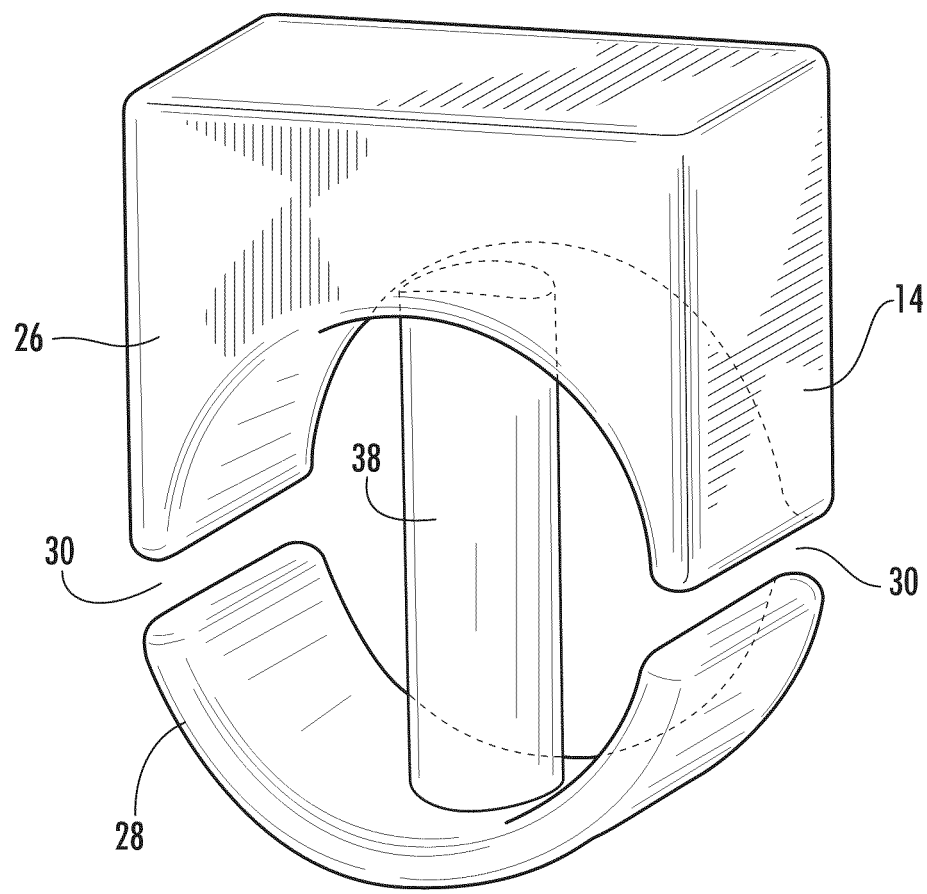
FIG. 3A shows a transparent isometric view of an alternative configuration of the reinforcing component ring portion of the spinal rod, the ring having at least one compression slit.
Figure 3B:
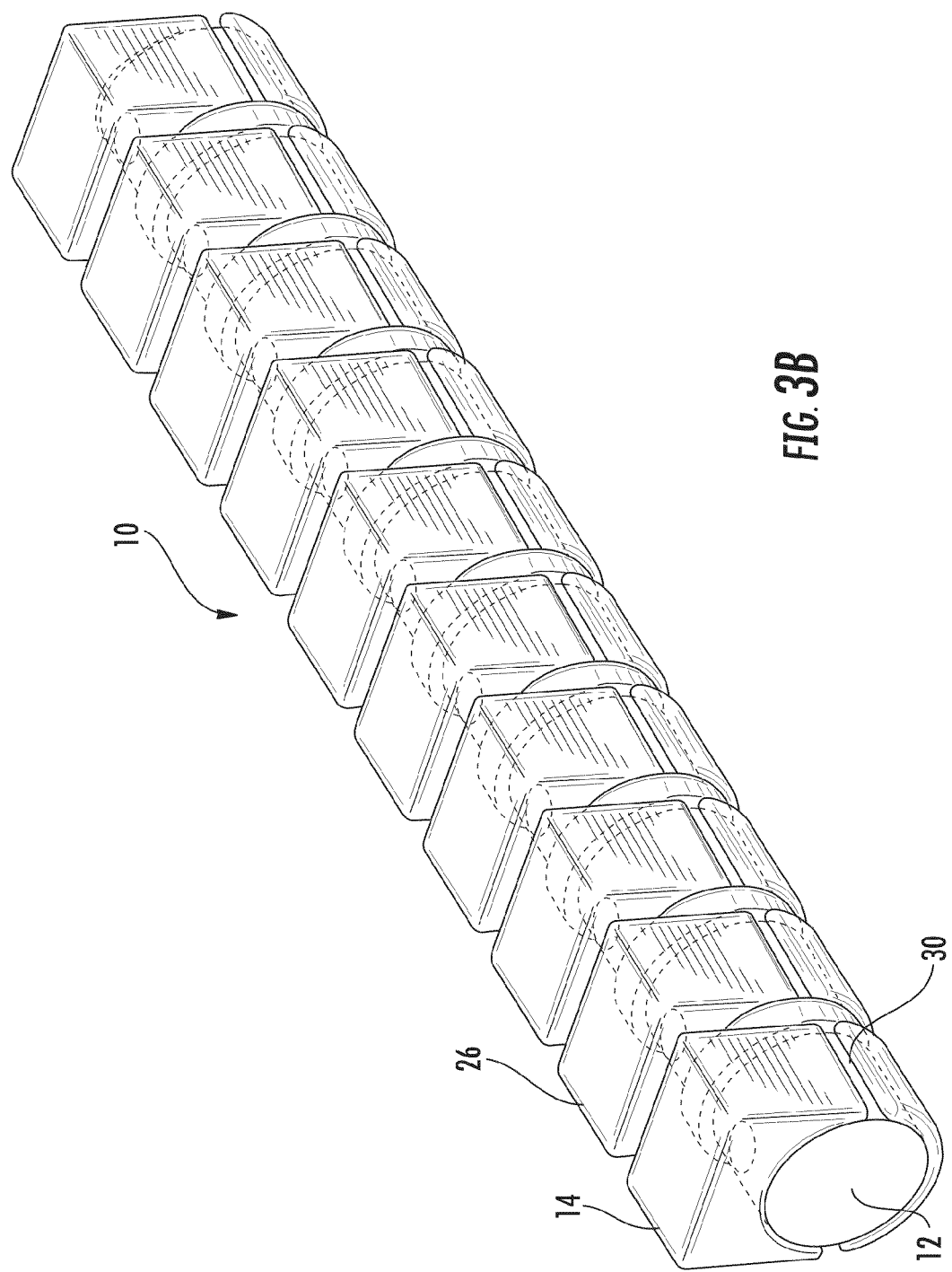
FIG. 3B shows the spinal rod with a plurality of the reinforcing component rings configured as shown in FIG. 3A.
Figure 3C:
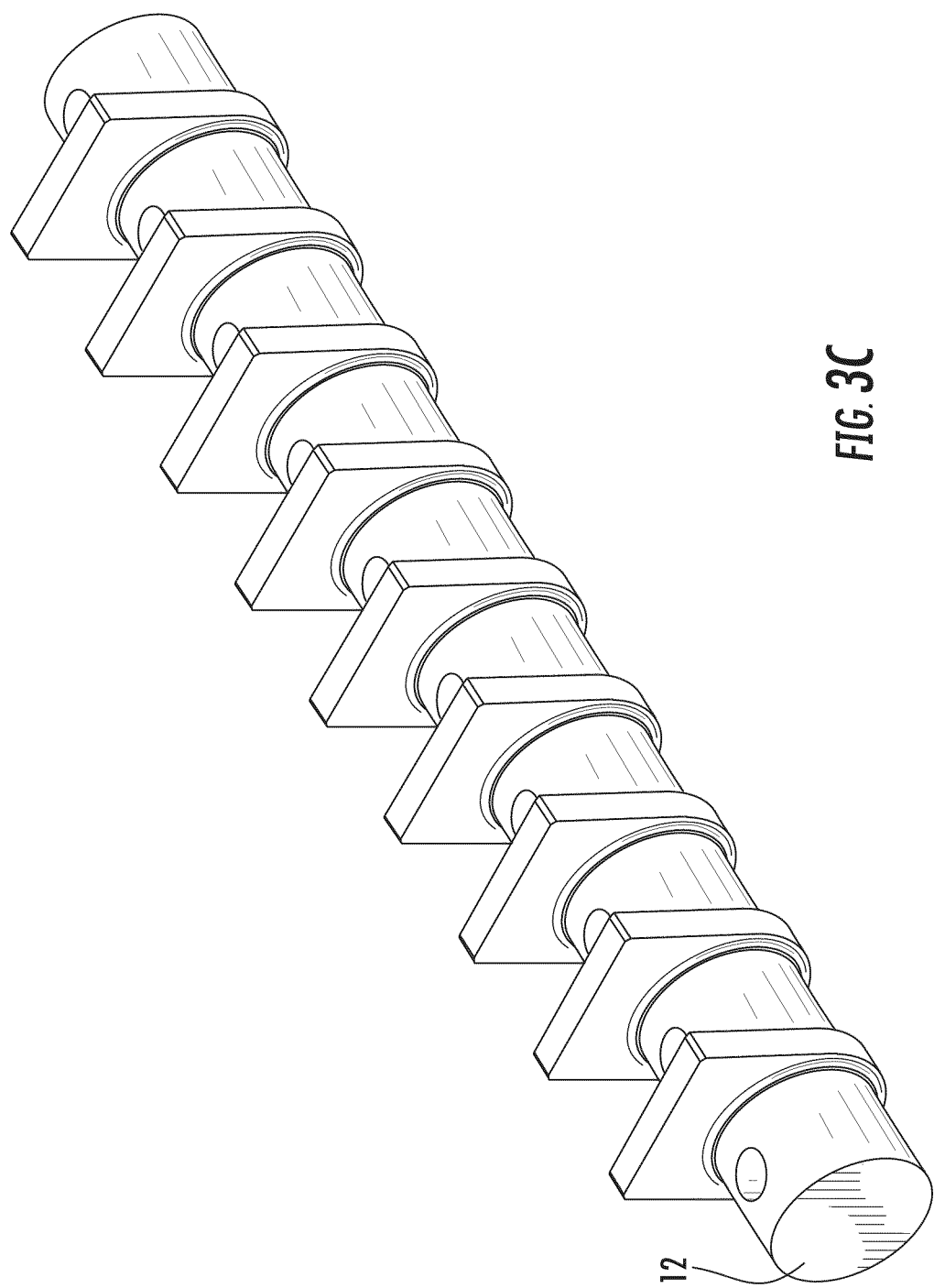
FIG. 3C shows an alternative flexible component of the spinal rod that may be used in place of the flexible portion shown in FIG. 3B.

Further, the collars 26 may be partially embedded into the flexible component 12, as shown in FIG. 2B or they may be imposed on top of the surface of the flexible component 12, as shown in FIG. 2C, giving an elevated appearance to the collar 26. When positioned on the outer surface 16 of the flexible component 12, the reinforcing component, such as a collar 26, may be provided with a beveled edge 28 along any edge of the reinforcing component 14 that may come into repeated and dynamic contact with the flexible component 12. Failure to provide a smoother beveled edge 28 could eventually subject the flexible rod 10 to unnecessary wear and material fatigue. An alternative embodiment of any of the possible collar 26 designs for the reinforcing component 14 may include a compression slit 30, which may effectively absorb a portion of the compressive forces exerted on the reinforcing component 14 that may result from the tightening of the set locking screw of the bone screw against the reinforcing component 14.

Alternatively, any of the embodiments of the composite spinal rod having the reinforcing component 14 disposed on the outer surface of the flexible component 12 may be manufactured such that the diameter of the flexible component 12 is slightly smaller than the internal diameter of the circumferentially positioned reinforcing component 14. In such an embodiment, the slight physical separation of the two components may provide additional protection of the flexible component 12 from the compressive forces placed against the external surface of the reinforcing component 14 when mechanical attachments such as pedicle screws are added.

Also contemplated are reinforcing components 14 that may be manufactured and incorporated into the composite spinal rod 10 in a configuration that is a combination of the longitudinally disposed reinforcing members 14, such as shown in FIG. 1A, and the circumferentially disposed reinforcing components 14. Such a combined configuration could present as a checkerboard, lattice, or matrix type array on the surface 16 of the flexible component 12. The capacity to manufacture the spinal rod 12 with a wide variety of reinforcing component 14 dispositions is advantageous because the manufactured configurations may be purposely varied so as to affect the functional characteristics of the spinal rod 10.

Figure 6:
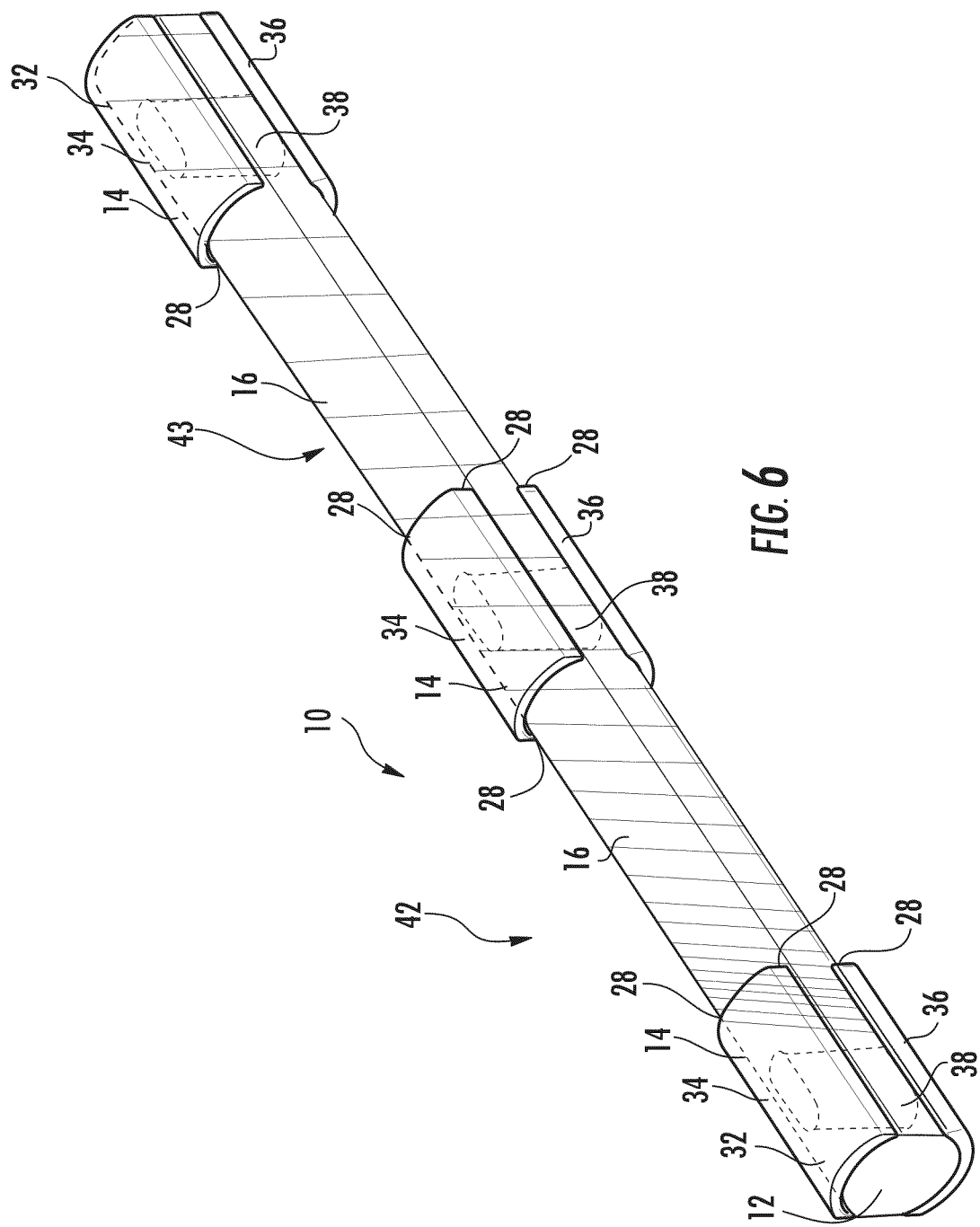
FIG. 6 shows the spinal rod having a flexible component that has a gradient of flexibility along all or at least a portion of its entire length.

Further, as graphically illustrated by the hash marks of greater frequency 42 or lesser frequency 44 in FIG. 6, the spinal rod may be manufactured so as to provide a flexible component 12 that is more stiff 42 or more flexible 44 at any selected position along the length of the rod 10. This alternative feature of the spinal rod 10 may thus provide a gradient of stress protection in selected sections of the rod. This may be accomplished by a variety of manufacturing techniques that affect the flexible component 12, the reinforcing component 14, or both in the same composite spinal rod 10. One means of creating a gradient of stress protection within the flexible component 12 is to manufacture the flexible component 12 to include short or chopped filament carbon fiber reinforcement in measured degrees only in those areas of the rod where such additional support is desired. Alternatively, carbon fibers may be circumferentially wound around the longitudinal axis of the spinal rod and structurally incorporated into the flexible component 12. The stress gradient can be varied by the introduction of additional winds of the carbon filaments in some areas as compared to other areas having fewer winds of the filaments and thus more flexibility.

A gradient of flexibility may be provided by varying the composition chemical formulation of the flexible component to provide either more stiffness or more flexibility as desired for different portions of the spinal rod 10.

A gradient of compressive stress protection may also be provided by manufacturing the outwardly positioned reinforcing component 14 as a tapered structure that is thicker in those areas where additional stress protection is desired and relatively thinner in those areas where more flexibility is desired and less stress protection is required.

FIGS. 4A-F show non-limiting examples of a further embodiment of the reinforcing component 14 of the spinal rod 10. These reinforcing components 14 may be described as reinforcing brackets 32. Common to any of the reinforcing brackets 32 shown in these figures is an upper bracket 34 and an opposing lower bracket 36, which are connected one to another by a connecting pin 38 that may pass transversely through the body of the flexible component 12. As with any of the reinforcing components 14 that were above discussed, the reinforcing bracket 32 may serve to protect the flexible component 12 from the compressive forces of the set screws that lock the spinal rod into the groove of a conventional bone screw. The connecting pin 38 may serve to transmit any such compressive forces from the upper bracket 34, which may be in contact with the set screw of the bone screw, to the lower bracket 36, thus protecting the internally disposed flexible component 12 from damage.

Figure 4A:
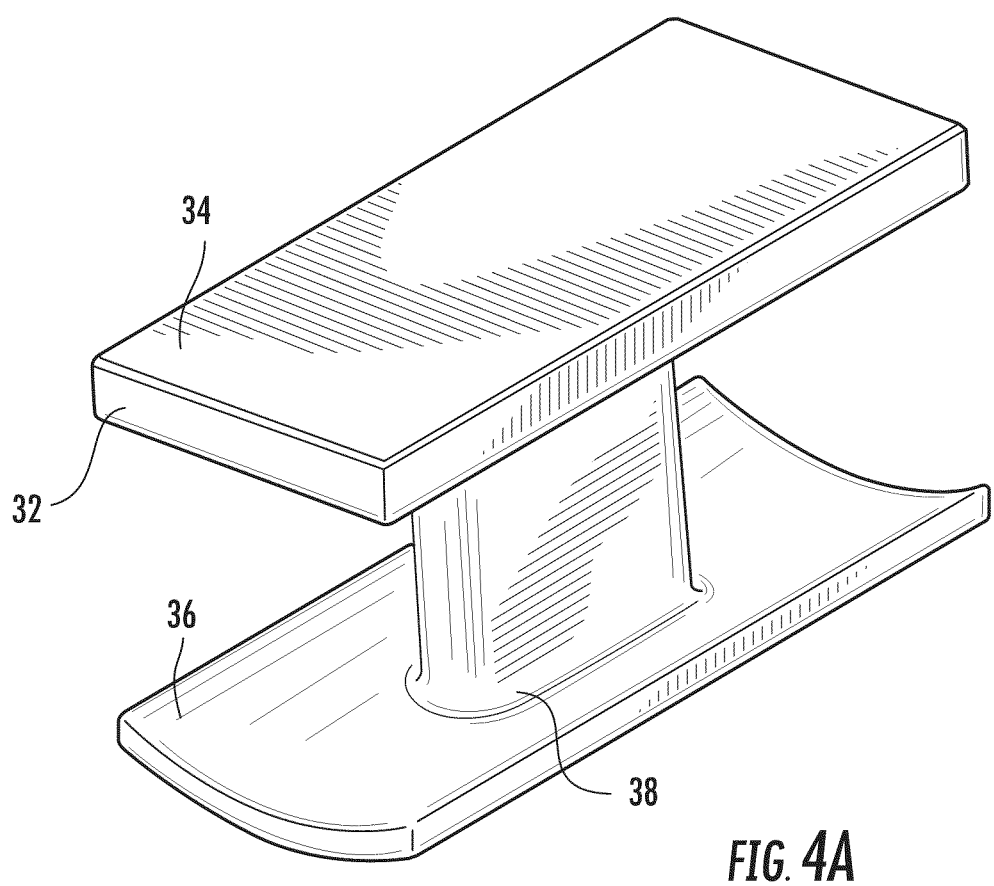
FIG. 4A shows an alternative reinforcing component ring portion of the spinal rod. The reinforcing component ring may be provided with at least one compression slit and as shown may have a flattened upper surface to facilitate contact with the locking set screw of a conventional bone screw that may be attached at that position.
Figure 4B:
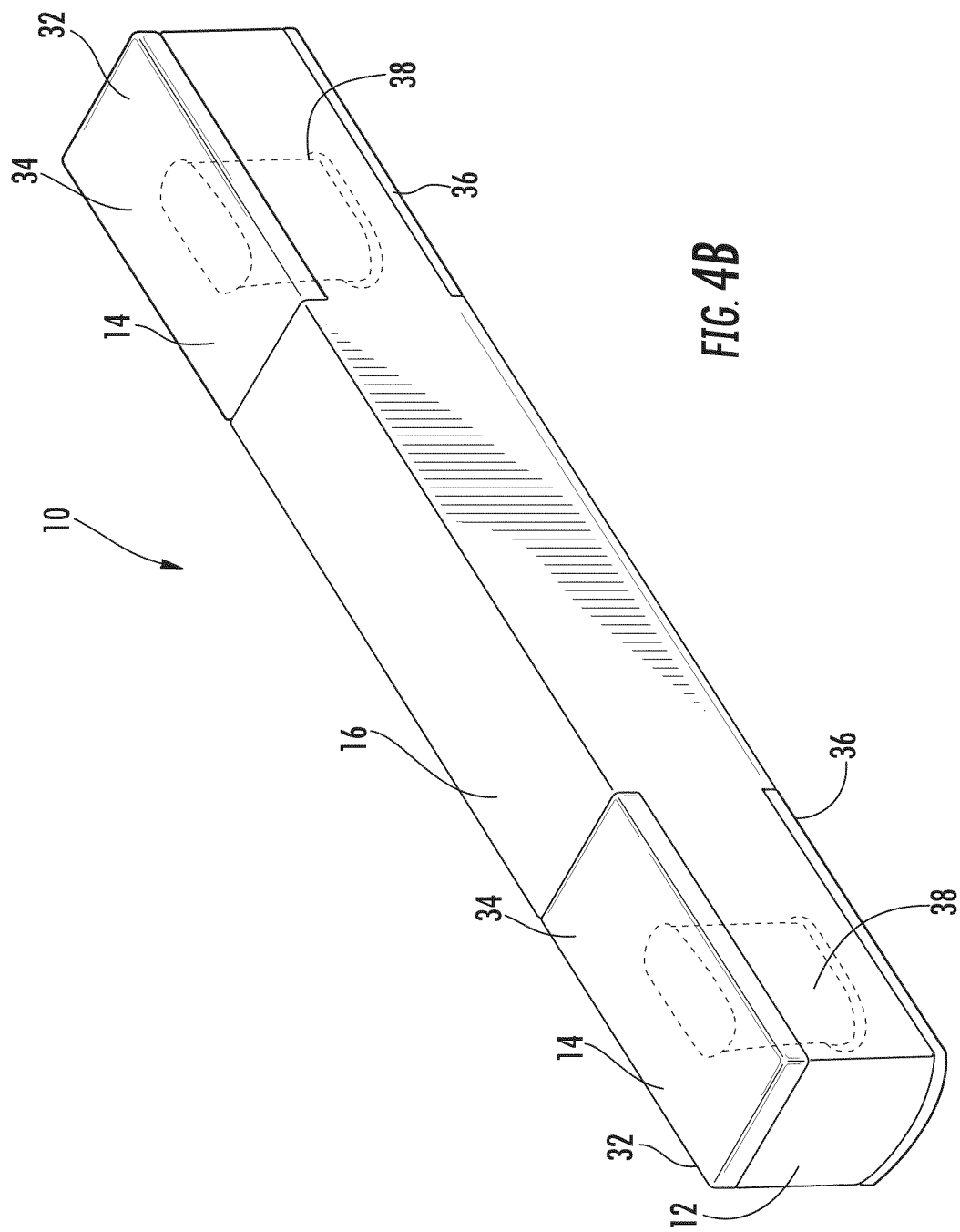
FIG. 4B shows the alternative reinforcing component ring of FIG. 4A partially embedded in a flexible component of the spinal rod, the rod being configured to have a flattened upper surface and a curved lower surface.

As shown in FIGS. 4A-B, the reinforcing bracket 32 may be configured to have a flat upper bracket 34, which may be better suited to receiving contact with a locking device of a pedicle screw. One non-limiting example of a well known locking device is the locking set screw of a pedicle screw. The area of the reinforcing component 14 where the pedicle screw locking device may make contact with the reinforcing component 14 of the spinal rod 10 may be textured, brazed, dimpled, cross-hatched, chemically treated or machined in any way commonly known in the art to provide a roughened surface that will facilitate the contact hold of the pedicle screw locking device on the surface of the spinal rod 10. A benefit to improving the frictional hold between the locking device and the surface of the reinforcing component 14 may be that the same effective hold may be achieved with a lessened level of compressive force of the locking device against the spinal rod 10. Thus, the provision of this alternative feature of a roughened surface may in addition to improving the holding power of the locking device against the spinal rod 10, may also serve to protect the flexible component 12 of the spinal rod 10 from greater levels of compressive force.

Figure 4C:
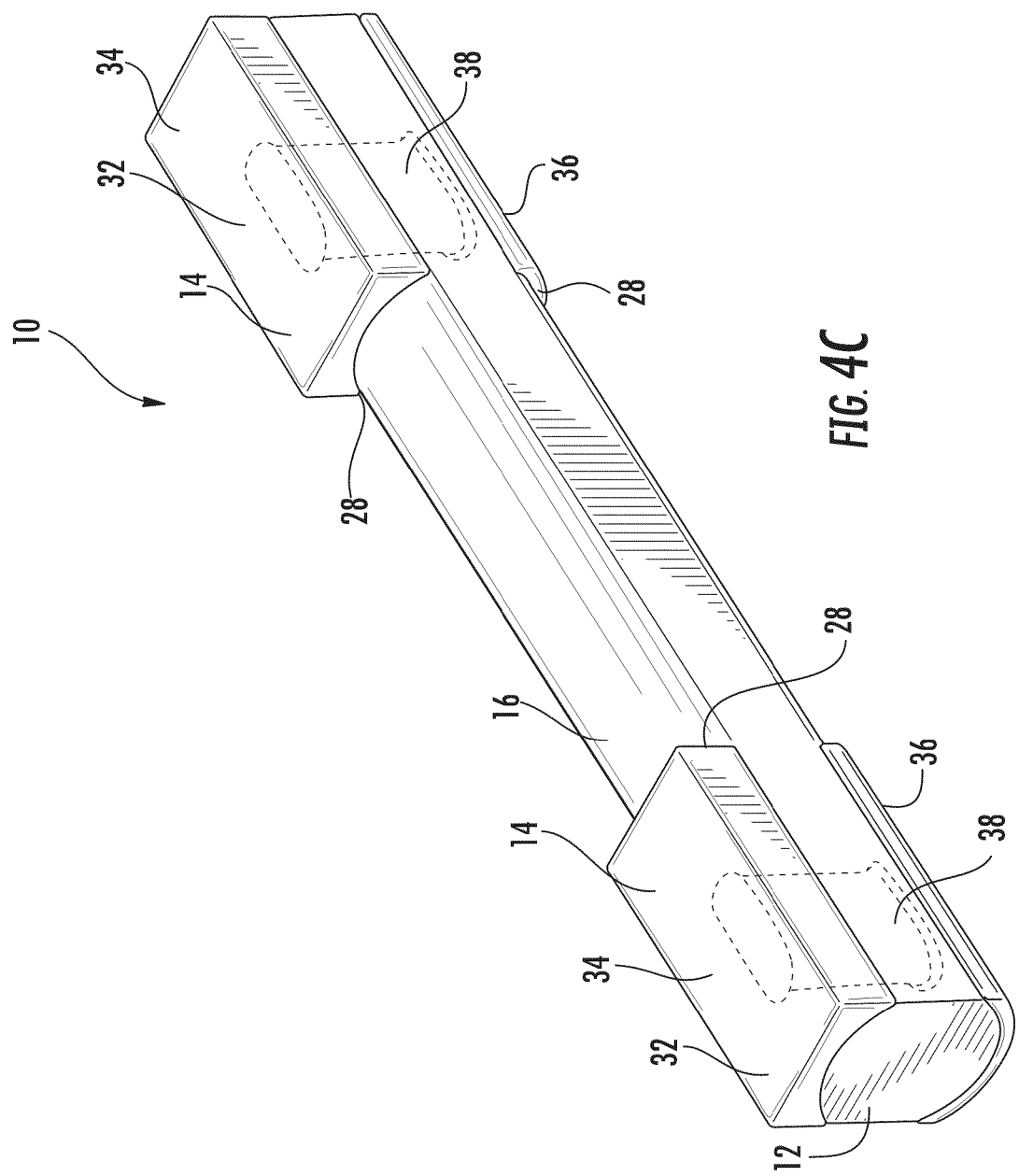
FIG. 4C shows an alternative configuration of the spinal rod shown in FIG. 4B with the reinforcing component ring disposed in an elevated position over the surface of the flexible portion of the rod.
Figure 4D:
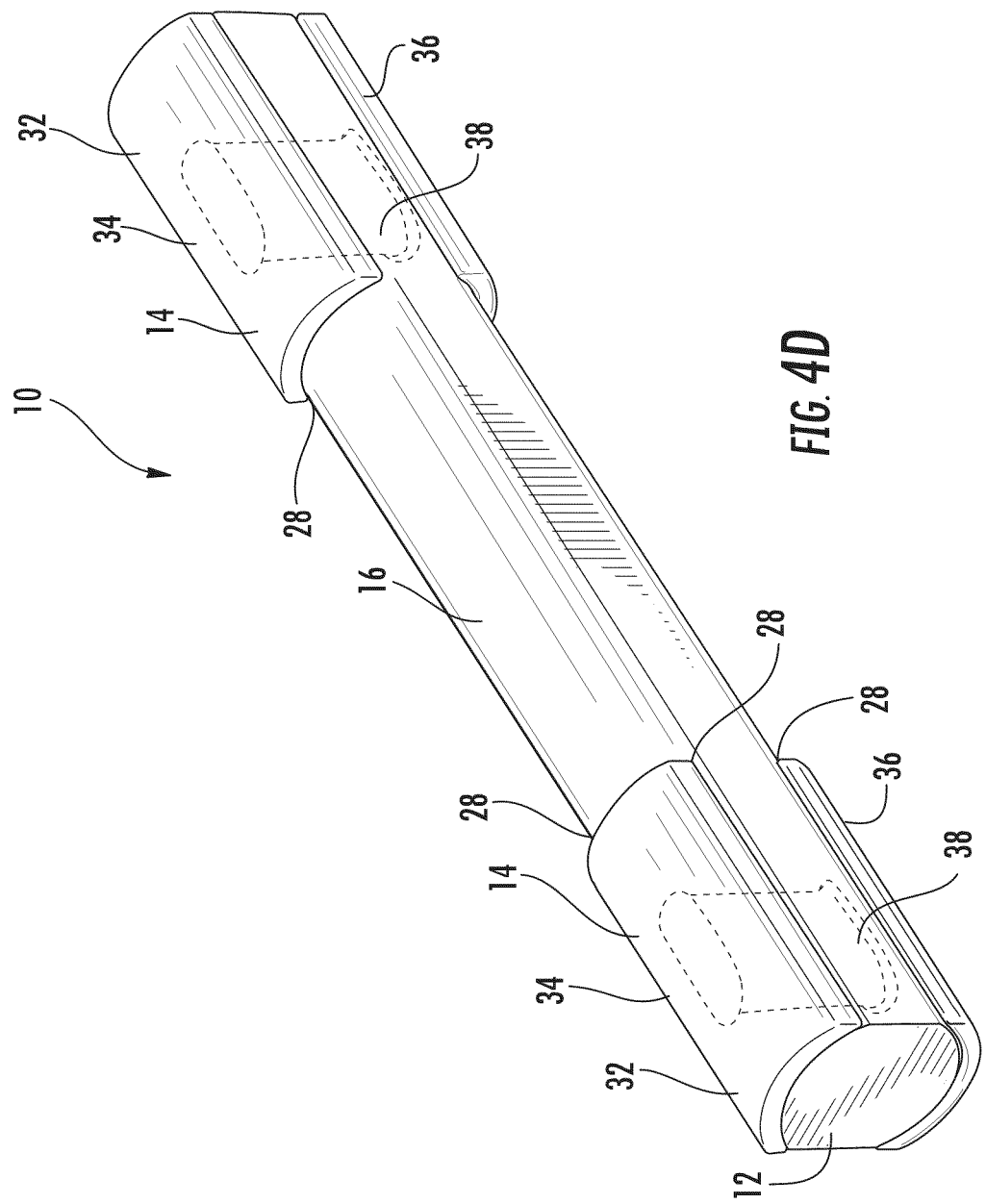
FIG. 4D shows an alternative configuration of the reinforcing component ring wherein the upper and lower portions are curved so as to conform to the curved upper and lower surfaces of the flexible portion of the rod.
Figure 4E:
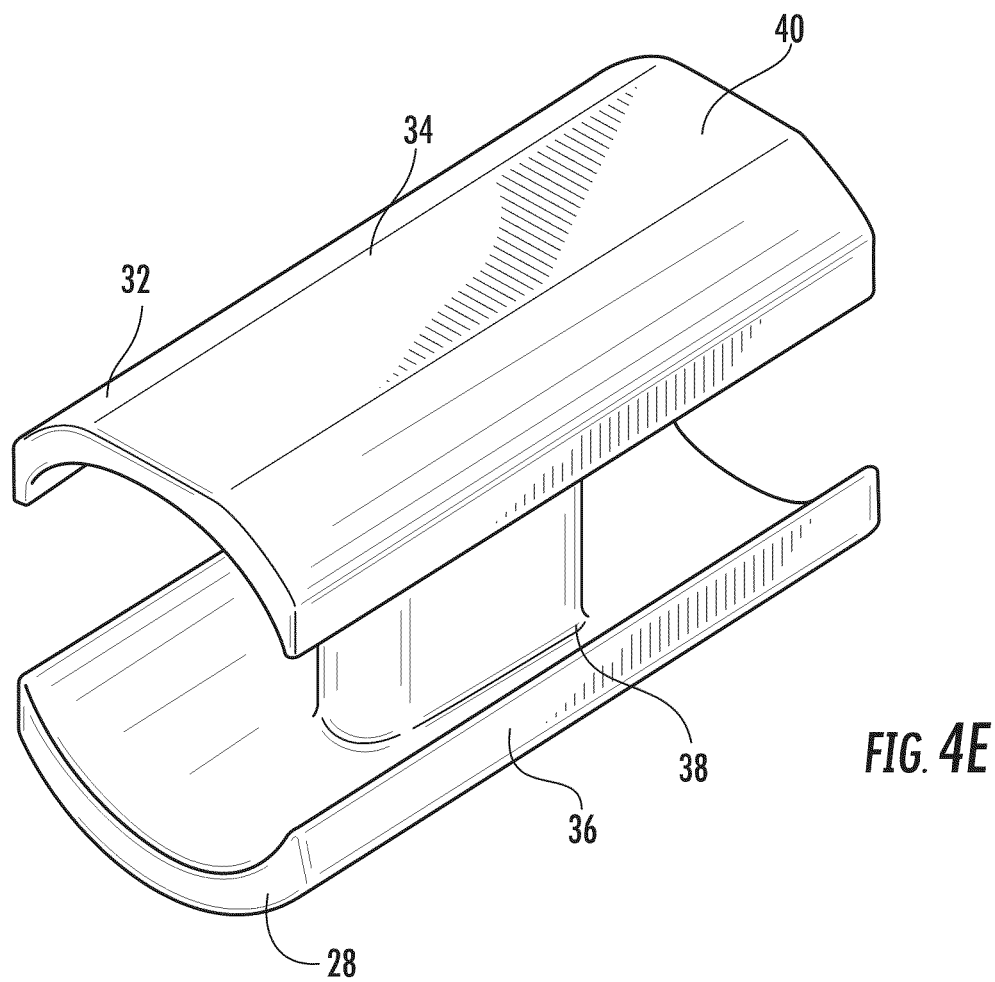
FIG. 4E-F show respectively an alternative reinforcing component ring having upper and lower portions that are curved, the upper curved portion being partially flattened to facilitate attachment of a set screw locking a bone screw to the rod and, in FIG. 4F, a pair of the same alternative reinforcing component rings mounted in an elevated position over the surface of the flexible portion of the rod.
Figure 4F:
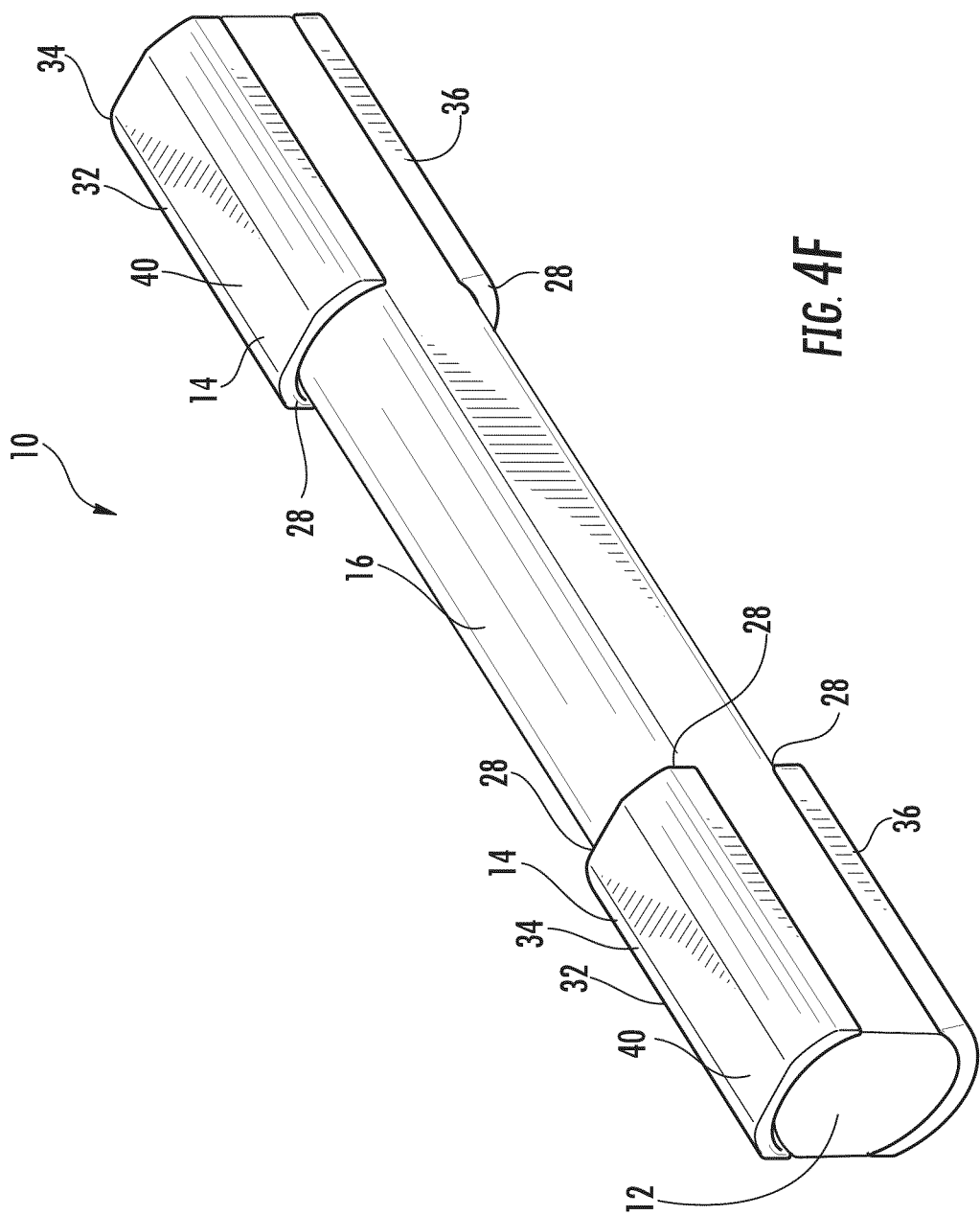

As shown in FIG. 4B, the reinforcing bracket may be partially embedded in the flexible component 12 to provide an appearance of being flush mounted on the outer surface 16 of the flexible component 14. Alternatively, the reinforcing bracket 32, as shown in FIGS. 4C, 4D, and 4F, may extend above the outer surface 16 on the flexible component 12. Another variation of the reinforcing bracket 32 is shown in FIGS. 4E-F as having curved upper bracket 34 with a flattened apex that may best be described as an upper bracket platform 40. Any of these exemplary variations of the bracket-type reinforcing component 14 may be employed to meet the specific needs of the surgeon without departing from the basic concept of providing a flexible composite spinal rod that is protected from damage from the compressive forces associated with attachment to a pedicle screw.

Figure 5:
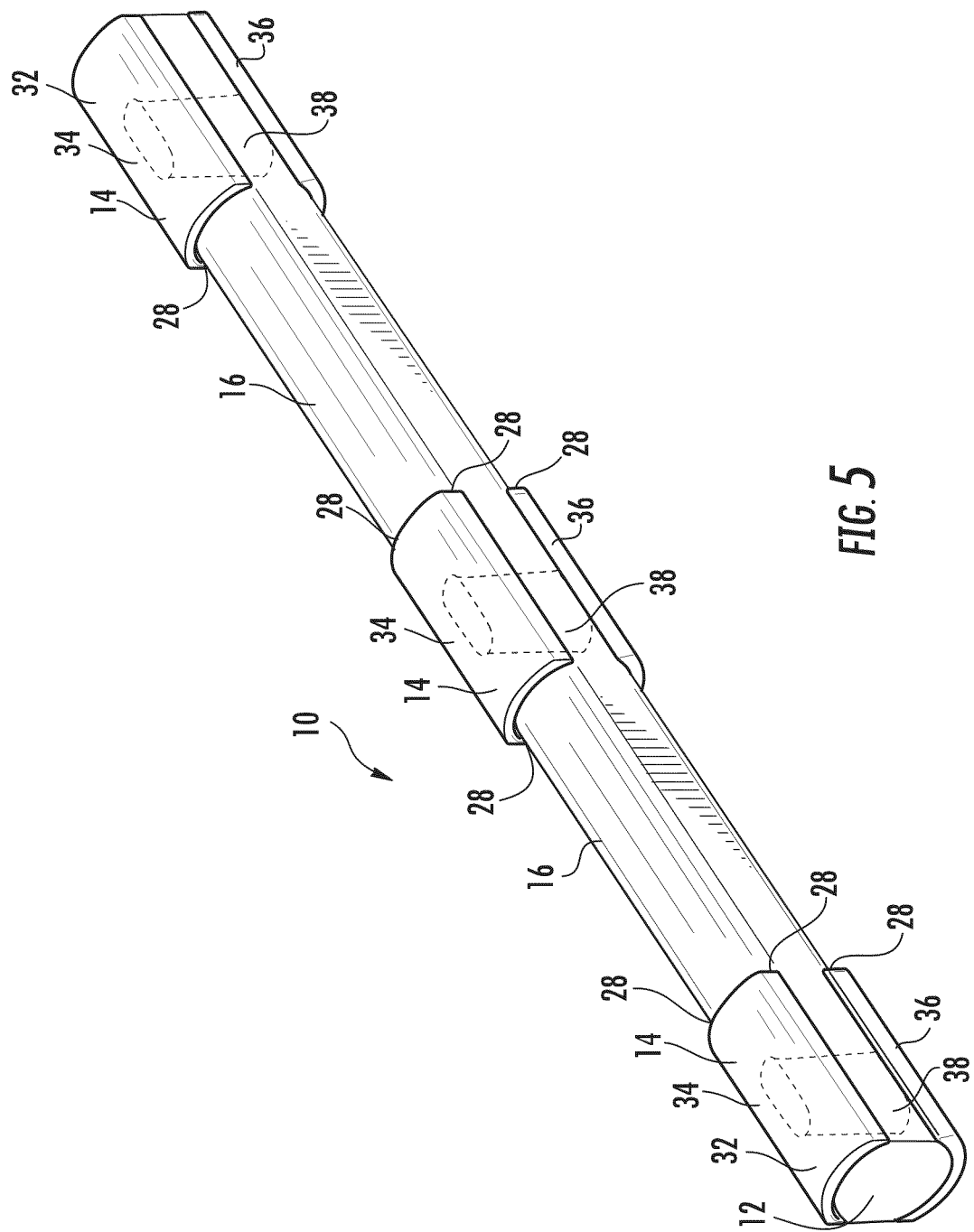
FIG. 5 shows the use of rigid reinforcing components positioned at multiple levels along the flexible portion of the rod.
Figure 7:
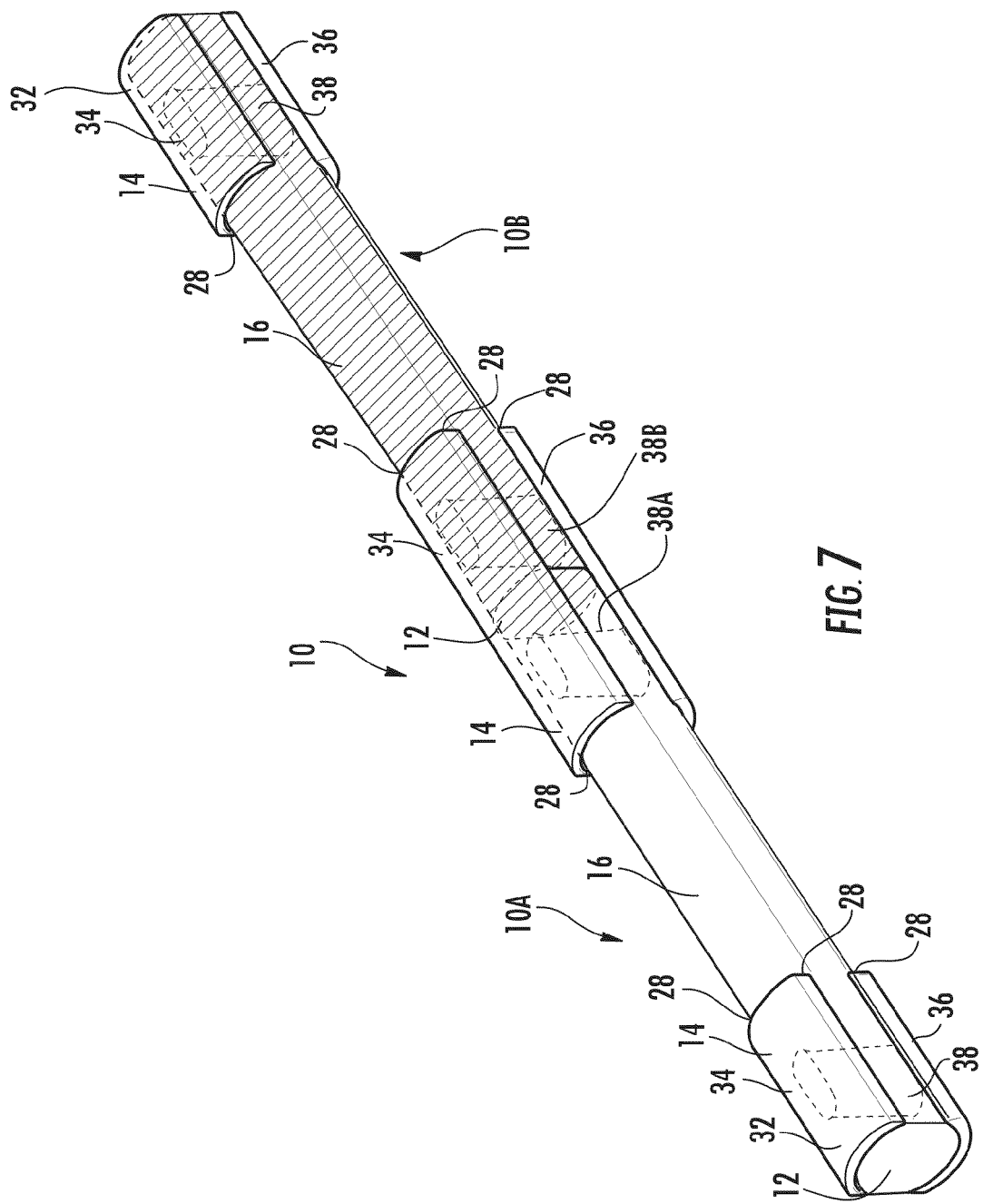
FIG. 7 shows the spinal rod having an alternative embodiment of the rigid reinforcing component, wherein the reinforcing component is configured to serve as a connector between two longitudinally aligned flexible components of a rod, the two connected flexible components having the same or different degrees of flexibility.

As shown in FIGS. 5, 6 and 7, the rigid reinforcing components 14 may be positioned at multiple levels. Such a multi-level construct may be provided with a consistent degree of flexibility and compressive stress resistance or it may be provided with any or a combination of the alternative configurations and compositions discussed above. In manufacturing the spinal rod 10, the gradient of flexibility in the flexible component 12 may be provided as varying or consistent at any specific portion of the spinal rod as required by the functional needs of the construct.

Figure 8A:
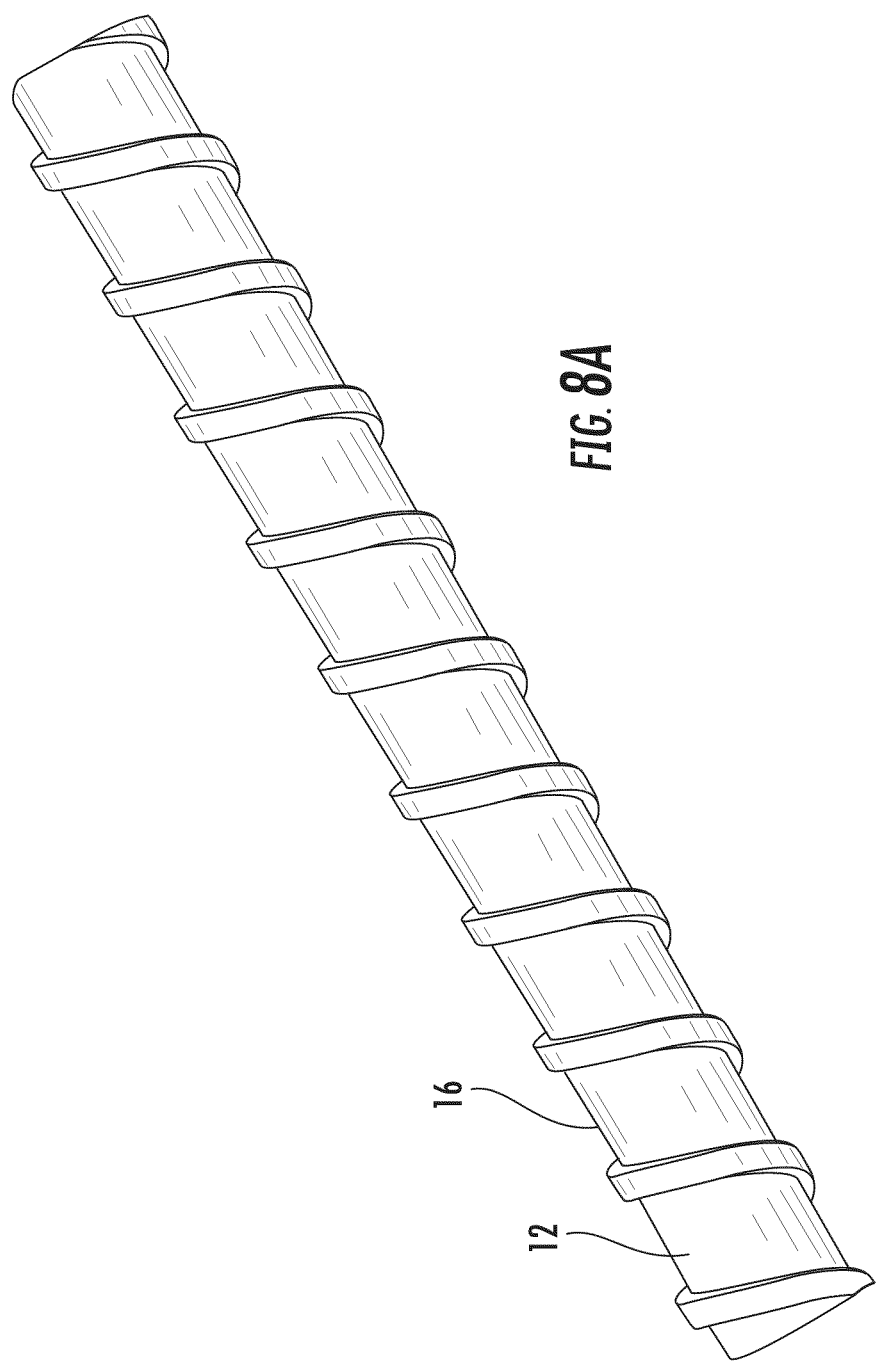
FIG. 8A-B show respectively a flexible portion and a reinforcing component portion of an alternative embodiment of the spinal rod, wherein the two portions are configured to have a corresponding spiral slit and spiral ridge that can engage when the two portions of the rod are assembled together.
Figure 8B:
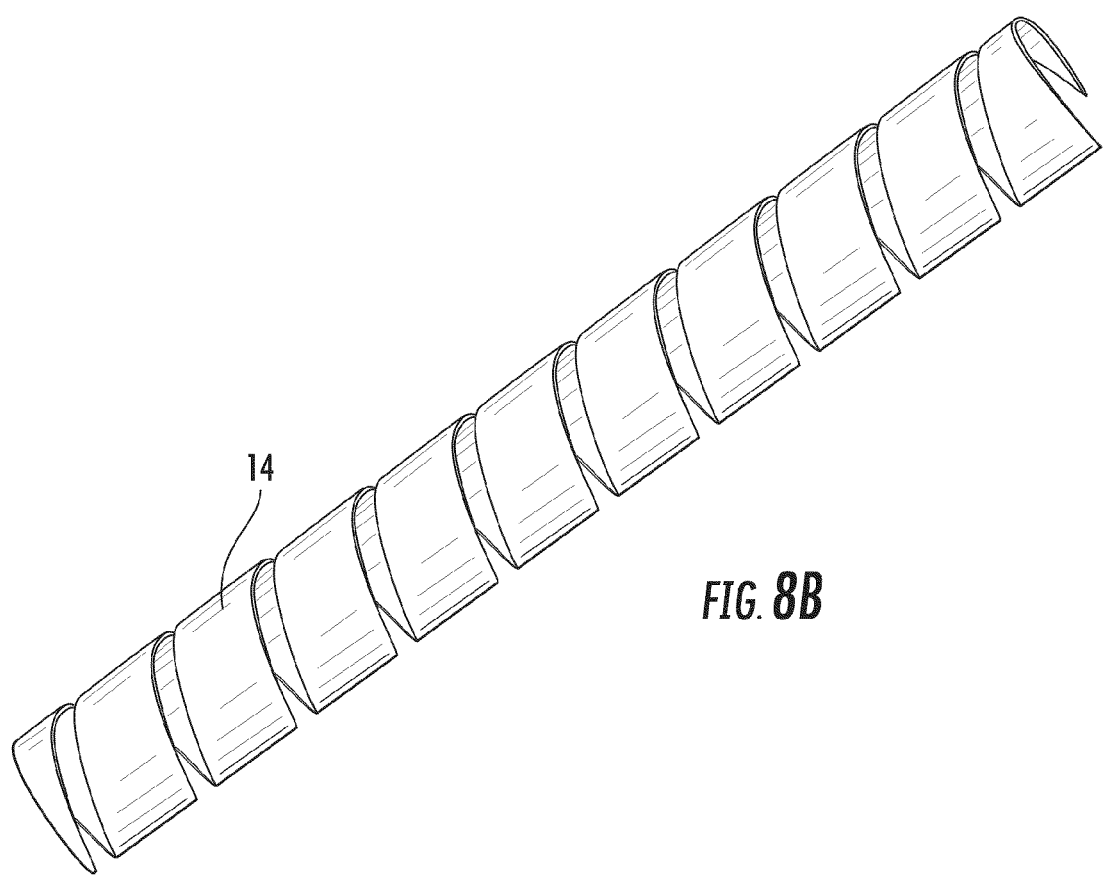

Further, as shown in FIG. 7, the reinforcing component 14 may be configured to provide an end-to-end connection function between two or more separate flexible components 12 of the spinal rod 10. To provide protection against compressive forces and to strengthen the connection function embodiment 46, the reinforcing component 14 may be provided with multiple connecting pins 38A, 38B that pass transversely through the body of each of the two flexible component rods 10A, 10B to be connected end-to-end. As graphically illustrated by the hash marks 42 on flexible component rod 10B, the so connected flexible component rods 10A and 10B can have different compositions or functional characteristics. For example, one may have greater flexibility than the other due to its composition formulation or it may have differently configured internally disposed reinforcing components. Any of the exemplary embodiments discussed herein may be so connected one to the other as necessary to obtain the functional characteristics required for the spinal construct. FIGS. 8A-B show an additional embodiment of the spinal rod 10 wherein the reinforcing component 14 is configured as an open spiral having a complementary shape and size to the internally disposed closed spiral configuration of the flexible component 12. The spiral or thread design of the two components may facilitate the process of threading the two together to form the completed composite spinal rod 10. As with other embodiments, any other suitable manufacturing technique, such as extrusion of the PEEK into the reinforcing component 14, may also be employed. By varying the width of the grooves in the open spiral of the reinforcing component 14, or by varying the thickness of the reinforcing component 14 spiral, the manufacturing process can also be used to selectively determine the degree of stiffness and flexibility of the resulting spinal rod 10.

FIGS. 9 and 10A-D provide additional non-limiting examples of preferred embodiments. FIG. 9 demonstrates the possible use of a flat metal spring design for the reinforcing component 14. Within the spring design of the reinforcing component 14 the flexible component 12 may be allowed flexibility and protection from compressive forces as in other embodiments discussed herein. The spring-type reinforcing component 14 may be positioned with a complementary shaped groove in the outer surface 16 of the flexible component 12 or alternatively like on the surface of the flexible component 12. Even if a metal reinforcing component 14 is wound over flexible component 12, the outer diameter of the reinforcing component 14 may be greater than the diameter of the flexible component 12 so that only metal contacts the pedicle screw or other associated mechanism. In addition, the rod need not be round, as shown in FIG. 9, but may be a different shape, such as, for example, oval, octagonal or hexagonal. The use of metal end caps 22 are also shown in FIG. 9. In practice, end caps 22 may be attached to any of the embodiments of the present technology.

Figure 10C:
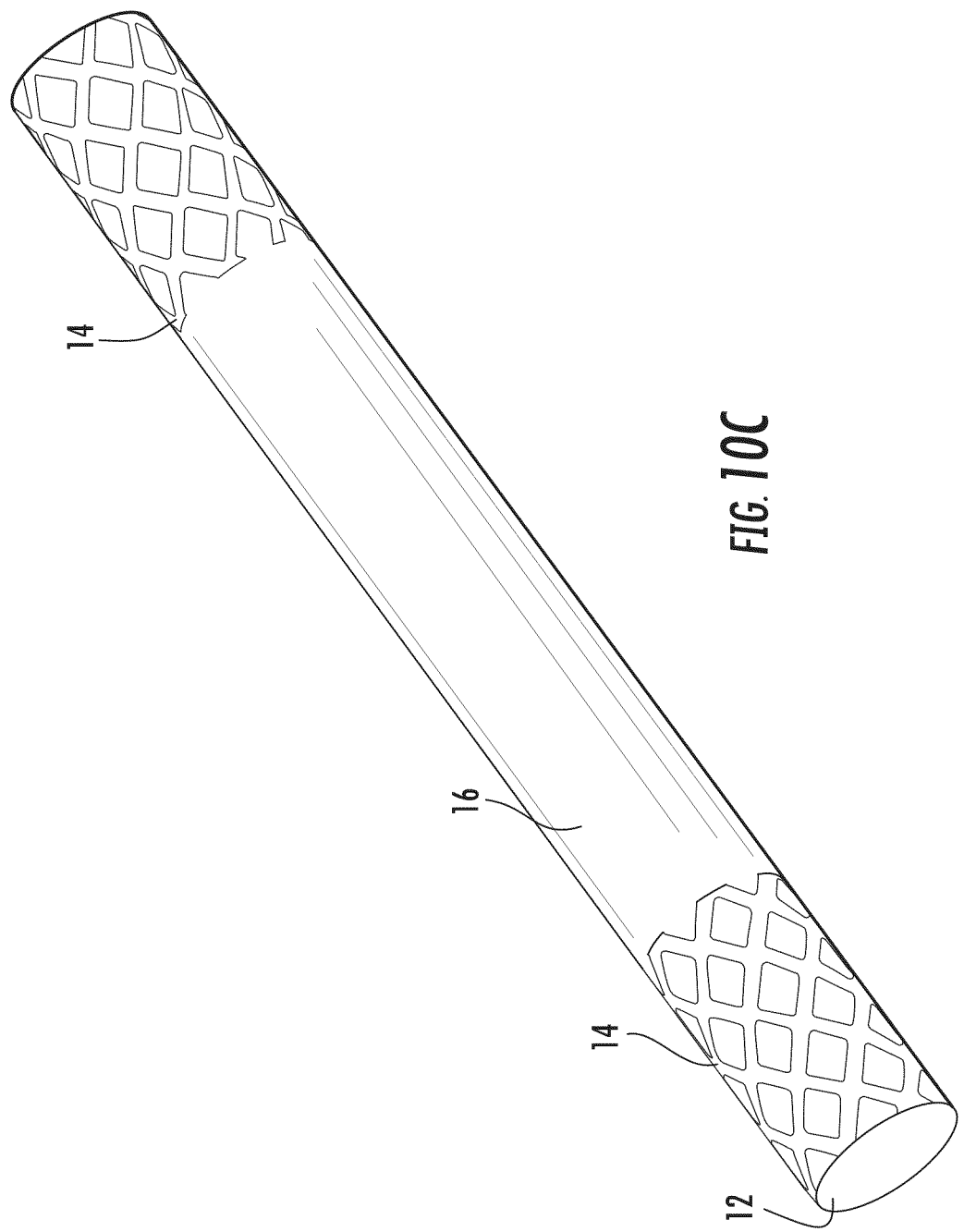
FIG. 10C shows the alternative reinforcing component and flexible portion of FIG. 10B, wherein the reinforcing component mesh is disposed and partially embedded in only the end portions of the spinal rod.
Figure 10D:
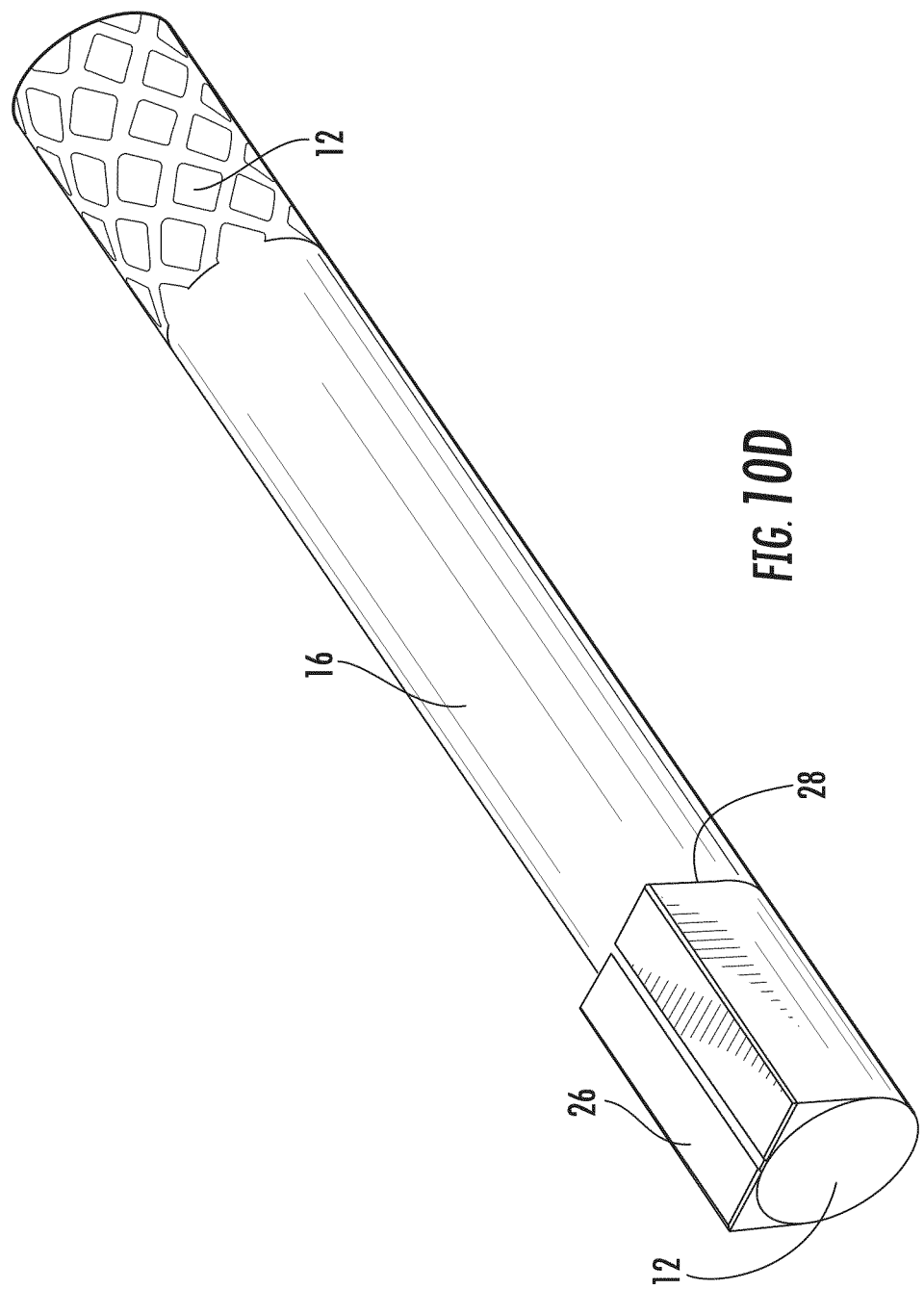
FIG. 10D shows an example of different alternative embodiments of the reinforcing component partially embedded in different portions of the same flexible portion of the rod.

FIGS. 10A-D show another embodiment of the reinforcing component 14 in the form of a protective mesh that is circumferentially disposed around the flexible component 12. The stiffness of the mesh reinforcing component 14 may be matched to the stiffness of the PEEK material selected for use in the flexible component 12, thus creating a uniform spinal rod 12. This matching and careful selection of manufacturing materials for all exemplary embodiments discussed herein may be employed to provide a customized composite spinal rod for a wide variety of applications. For example, as shown in FIG. 10D, multiple embodiments of the reinforcing component may be used on the same rod for optimal clinical applications.

The material strength of the spinal rod 10 may be used as a basis to determine with precision what degree of torque and downward pressure of the set screw is needed to firmly hold the spinal rod 10 in place in a pedicle screw without imposing excessive and potentially damaging compressive forces. For each construct, such a force determination may be made and then subsequently applied to the insertion tool used to attach the spinal rod to a pedicle screw.

The spinal rod 10 may be manufactured as integral components by methods known in the art, to include, for example, molding, casting, forming, extruding, or machine processing. The components may be manufactured using materials having sufficient strength, resiliency, and biocompatibility as is well known in the art for such devices. By way of example only, suitable materials may include implant grade metallic materials such as titanium, cobalt chromium alloys, stainless steel, or other suitable materials for this purpose. Flexible component 12 materials may be PEEK, carbon fiber reinforced PEEK, or any other suitable flexible and biocompatible material known in the art.

In another embodiment of the invention a kit may be provided. A kit may include at least one of the spinal rod and at least two pedicle screws. Spinal rods 10 of different lengths, diameters, and cross sectional shapes may be provided in the kit to permit selection and substitution as deemed necessary. Additionally, a kit may include tools and/or instruments suitable to facilitate implanting the spinal rod 10. Such a kit may be provided with sterile packaging to facilitate opening and immediate use in an operating room.

Although the invention herein has been described with reference to particular embodiments, it is to be understood that these embodiments are merely illustrative of the principles and applications of the present invention. It is therefore to be understood that numerous modifications may be made to the illustrative embodiments, and that other arrangements may be devised, without departing from the spirit and scope of the present invention as defined by the appended claims.

The invention claimed is:

1. A kit for use in connecting and stabilizing adjacent vertebrae, the kit comprising:
   a spinal rod including:
      an elongated flexible component including a monolithic body comprised of a first material, the body defining an aperture extending through the body, and
      a reinforcing component comprised of a second material that is more rigid than the first material, the reinforcing component being resistant to damage from compressive forces;
      wherein the reinforcing component comprises an upper bracket, an opposing lower bracket, and a connecting pin extending therebetween, and
      wherein the connecting pin is disposed within the aperture of the body such that it is disposed transversely through the body of the flexible component; and
   at least one pedicle screw, each pedicle screw including a screw portion and a locking set screw,
   wherein, when the spinal rod is connected to the at least one pedicle screw, the reinforcing component is compressed between the screw portion and the locking set screw of at least one of the pedicle screws.

2. The kit of claim 1, wherein each end of the connecting pin is directed toward one of the upper bracket and the lower bracket, at least one of the upper bracket and the connecting pin or the lower bracket and the connecting pin defining a compression space.

3. The kit of claim 1, wherein at least one of the upper bracket and the lower bracket is at least partially embedded in a surface of the flexible component.

4. The kit of claim 1, wherein at least one edge of the upper and lower brackets is tapered, and wherein the tapered edge creates a gradient of compressive stress shielding for the underlying flexible component.

5. The kit of claim 1, wherein the reinforcing component is at least two separate reinforcing components.

6. The kit of claim 1, wherein the flexible component has a gradient of flexibility along at least a portion of its length.

7. The kit of claim 1, wherein the flexible component has a plurality of sections and wherein the flexibility of one section differs from the flexibility of at least one other section.

8. The kit of claim 1, wherein the spinal rod is multiple spinal rods and the at least one pedicle screw is multiple pedicle screws, the kit further comprising at least one instrument or tool associated with the use of the spinal rods and the pedicle screws.

9. The kit of claim 1, wherein the first material is selected from the group consisting of PEEK and carbon fiber reinforced PEEK, and wherein the second material is selected from the group consisting of metal and ceramic.

10. The kit of claim 1, wherein the upper bracket has a flat outer surface.

11. The spinal rod kit of claim 10, wherein the lower bracket has a curved outer surface.

12. The kit of claim 1, wherein the upper bracket is curved with a flattened apex.

13. The kit of claim 1, wherein an outer surface of the upper or lower bracket is textured.

14. A method for connecting and stabilizing adjacent vertebrae, the method comprising:
   providing the kit of claim 1;
   providing a surgical field of view for insertion of the spinal rod;
   connecting the spinal rod to adjacent vertebrae.

15. The method of claim 14, wherein the connecting step includes connecting pedicle screws to vertebrae and connecting the pedicle screws to the spinal rod.

16. The method of claim 15, wherein the pedicle screws are connected to the spinal rod at a position on the spinal rod where compressive forces imposed by the pedicle screws on the spinal rod are transferred via the reinforcing component transversely across the flexible component, wherein the reinforcing component provides stress shielding for the flexible component.

* * * * *

UNITED STATES PATENT AND TRADEMARK OFFICE
CERTIFICATE OF CORRECTION

PATENT NO.         : 9,017,384 B2
APPLICATION NO.    : 12/454187
DATED              : April 28, 2015
INVENTOR(S)        : Hyun Bae and Charanpreet S. Bagga Page 1 of 1

It is certified that error appears in the above-identified patent and that said Letters Patent is hereby corrected as shown below:

In the Claims

Column 14, line 19, after "The", delete "spinal rod".

Signed and Sealed this
Ninth Day of February, 2016

Michelle K. Lee
*Director of the United States Patent and Trademark Office*